US009388462B1

(12) United States Patent
Eltoukhy

(10) Patent No.: US 9,388,462 B1
(45) Date of Patent: Jul. 12, 2016

(54) DNA SEQUENCING AND APPROACHES THEREFOR

(75) Inventor: Helmy Eltoukhy, Woodside, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 1193 days.

(21) Appl. No.: 11/748,266

(22) Filed: May 14, 2007

Related U.S. Application Data

(60) Provisional application No. 60/799,769, filed on May 12, 2006.

(51) Int. Cl.
*C12Q 1/68* (2006.01)
*C12Q 1/66* (2006.01)
*G01N 21/76* (2006.01)

(52) U.S. Cl.
CPC ............... *C12Q 1/6869* (2013.01); *C12Q 1/66* (2013.01); *G01N 21/76* (2013.01); *Y10T 436/143333* (2015.01); *Y10T 436/166666* (2015.01)

(58) Field of Classification Search
USPC .......................................................... 435/94
See application file for complete search history.

(56) References Cited

U.S. PATENT DOCUMENTS

| 5,527,675 A * | 6/1996 | Coull et al. ..................... 435/6 |
| 6,303,303 B1 * | 10/2001 | Green et al. ..................... 435/6 |
| 6,681,186 B1 * | 1/2004 | Denisov et al. ................ 702/20 |
| 2002/0147548 A1 * | 10/2002 | Walther ............. G01N 30/8624 702/20 |
| 2003/0120471 A1 * | 6/2003 | Izmailov .......... G01N 27/44717 703/11 |

OTHER PUBLICATIONS

Svantesson et al. ("A mathematical model of the Pyrosequencing reaction system," Biophysical Chemistry 2004, 110, 129-145).*
Ewing et al. ("Base-Calling of Automated Sequencer Traces Using Phred. I. Accuracy Assessment" Genome Research 1998, 8, 175-185).*
Eltoukhy et al., "Modeling and Base-Calling for DNA Sequencing-by-Synthesis," 2006 IEEE International Conference on Acoustics, Speech and Signal Processing, vol. II, pp. 1032-1035, May 14-19, 2006.*
Eriksson, S. "Cytochrome P450 Genotyping by Multiplexed Real-Time DNA Sequencing with Pyrosequencing™ Technology," ASSAY and Drug Development Technologies, 2002, 1, 49-59.*
Brent Ewing and Phil Green. "Base-Calling of Automated Sequencer Traces Using*Phred*.?II.Error?Probabilities." Genome Research 8: 186-194 (1998).

* cited by examiner

*Primary Examiner* — Yelena G Gakh
*Assistant Examiner* — Michelle Adams
(74) *Attorney, Agent, or Firm* — Crawford Maunu PLLC

(57) ABSTRACT

Polymer sequencing is facilitated. According to an example embodiment of the present invention, a polymer sequencing approach is implemented using a multitude of polymer specimens for a particular polymer type is implemented. For each step in a polymer sequencing test, non-idealities are categorized using data obtained from the polymer sequencing test, and in response to the categorized non-idealities, a polymer sequence is identified for a corresponding step of the polymer sequencing test. With this approach, read lengths achieved with a particular polymer sequencing method can be improved.

17 Claims, 23 Drawing Sheets

(a)

(b)

DNA SEQUENCING AND APPROACHES THEREFOR

RELATED PATENT DOCUMENTS

This patent document claims the benefit, under 35 U.S.C. §119(e), of U.S. Provisional Patent Application No. 60/799,769, filed May 12, 2006 and entitled: "Polymer Sequencing and Approaches Therefor."

FEDERALLY-SPONSORED RESEARCH OR DEVELOPMENT

This invention was made with Government support under contract HG003571 awarded by the National Institutes of Health. The U.S. Government has certain rights in this invention.

FIELD OF THE INVENTION

The present invention relates generally to polymer sequencing, and more particularly to arrangements and approaches for polymer sequencing.

BACKGROUND

Polymer sequencing, such as protein sequencing or DNA sequencing, is susceptible to errors, misalignment and other issues related to inconsistent synthesis and/or cleavage as associated with polymers undergoing analysis. These issues can result in inaccurate analysis and other related issues.

One approach to synthesis-based sequencing is DNA sequencing-by-synthesis, which generally involves biochemical processes by which a target DNA strand is iteratively built up to determine its sequence. An example of such methods is Pyrosequencing, which offers the promise of high throughput and low cost sequencing via efficient mass parallelization and its relative simplicity. However, achieving reliable DNA read lengths using Pyrosequencing requires high reagent costs to maximize signal fidelity and thereby has often been prohibitively expensive for applications such as whole genome shot-gun assembly.

Recently, there has been great interest in developing cheaper, higher throughput de novo DNA sequencing technologies and protocols to jumpstart the next phase of genetic inquiry beyond the human genome project. Although much progress has been made in the last two decades, whereby sequencing cost has been reduced from tens of dollars per base to a few cents per base today, the cost of sequencing a single mammalian-sized genome is still in the tens of millions of dollars. This exorbitant cost greatly hinders such vital studies as comparative genomic analysis across species, detailed studies of human genetic variation, and analyses of difficult-to-culture microbial communities.

Microarray-based technologies can be used for single-nucleotide polymorphism (SNP) analysis; however, these genotyping methods are likely to miss rare differences that may be critical to diagnosing certain conditions as well as fail to extract long-range information, such as genomic rearrangements.

One sequencing approach is Sanger sequencing, which uses fluorescence detection of dideoxy terminated fragments resolved by capillary array electrophoresis (CAE). See, e.g., B. Ewing, P. Green, "Basecalling of automated sequencer traces using phred. II. Error probabilities," *Genome Research* 8, pp. 186-194, 1998. This method, first developed in 1977, now allows the sequencing of read segments of approximately 1000 nucleotides long with reasonable accuracy. However, despite the past and ongoing enhancements to existing CAE technology, under this regime, the lower limit in terms of cost per mammalian genome is intolerably excessive for many applications.

These and other characteristics have been challenging to polymer sequencing and related applications, for both sequencing-by-synthesis and cleavage approaches, for a variety of polymers such as proteins and DNA.

SUMMARY

The present invention is directed to overcoming the above-mentioned challenges and others related to the types of applications discussed above and in other applications. These and other aspects of the present invention are exemplified in a number of illustrated implementations and applications, some of which are shown in the figures and characterized in the claims section that follows.

Various aspects of the present invention are applicable to the sequencing of polymers in a manner that addresses differences among polymers analyzed for a particular sequencing approach. Such differences may result, for example, where a particular step in a synthesis or cleaving approach is not carried out with all polymers in a group of polymers undergoing analysis, or with different tests performed at different times for a particular type of polymer. In accordance with various example embodiments, results from sequencing tests are adjusted in consideration of these differences.

In one embodiment of the present invention, a method for polymer sequencing via a multitude of polymer specimens for a particular polymer type is implemented. For each step in a polymer sequencing test, non-idealities are categorized using data obtained from the polymer sequencing test, and in response to the categorized non-idealities, a polymer sequence is identified for a corresponding step of the polymer sequencing test.

In another embodiment, a method for DNA sequencing is implemented. Results from a DNA sequencing test are modeled as a noisy switched linear system parameterized by potential DNA sequences and respective DNA bases. Using the modeling, a DNA sequence is selected from the potential DNA sequences with respect to a probability of matching the test results.

Consistent with another embodiment, an apparatus is implemented for polymer sequencing via a multitude of polymer specimens for a particular polymer type. The apparatus has means for applying a polymer sequencing test to iteratively synthesize or cleave polymer bases. The apparatus has means for categorizing, for each iteration, the non-idealities using data obtained from the polymer sequencing test, and means for identifying a polymer sequence for a corresponding step of the polymer sequencing test using the categorized non-idealities.

Another embodiment of the present invention includes a system for polymer sequencing via a multitude of polymer specimens for a particular polymer type. A polymer sequencing device iteratively modifies a multitude of polymer specimens with respect to their polymer bases. Logic, for each iterative modification, categorizes the non-idealities for different ones of the multitude of polymer specimens using data from the polymer sequencing device. Logic, for each iterative modification and using the categorized non-idealities, identifies a polymer sequence for a corresponding step of the polymer sequencing test.

The above summary is not intended to describe each illustrated embodiment or every implementation of the present invention.

BRIEF DESCRIPTION OF THE DRAWINGS

The invention may be more completely understood in consideration of the detailed description of various embodiments of the invention that follows in connection with the accompanying drawings, in which.

Figure 1:
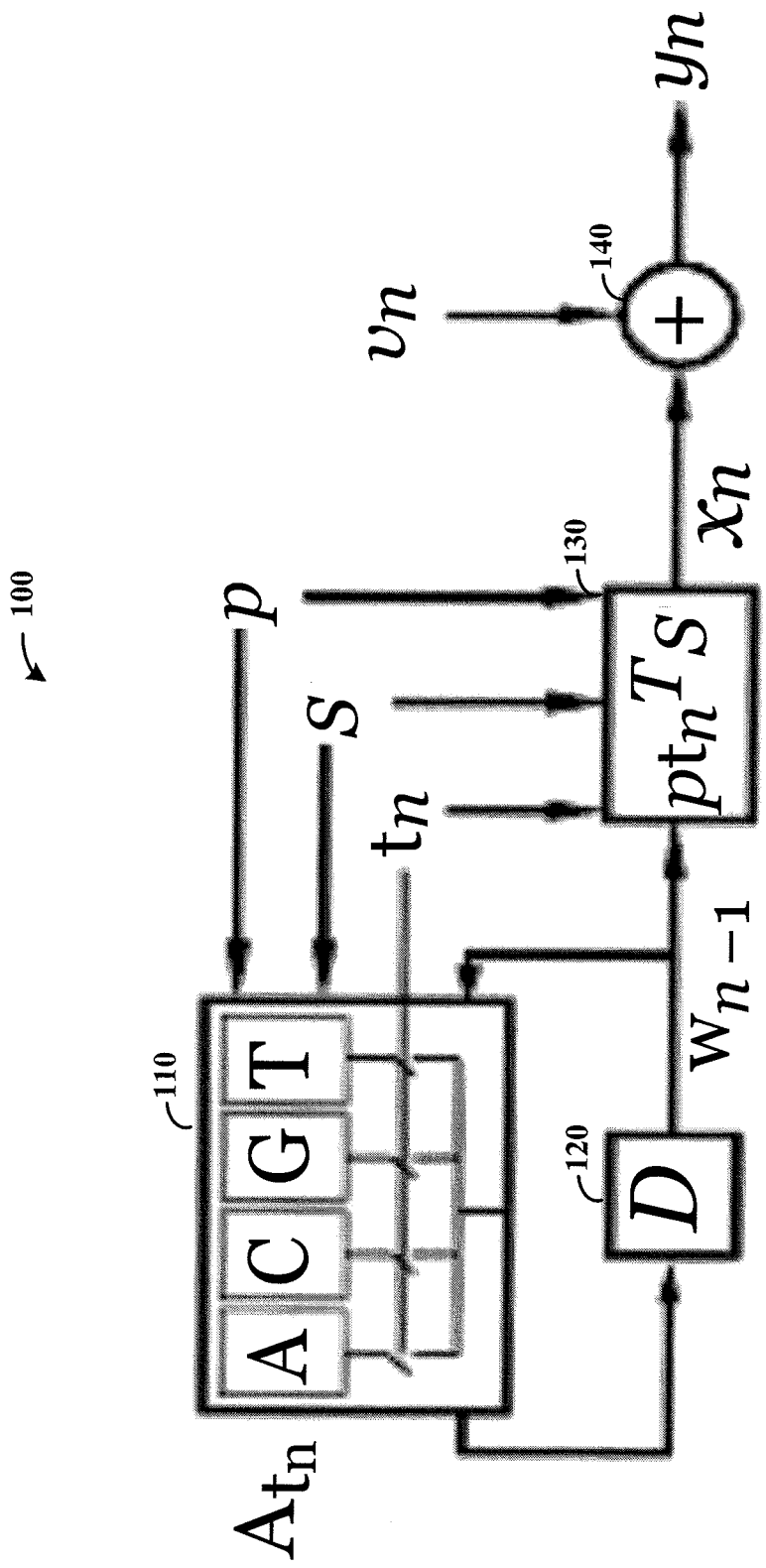
FIG. 1 shows a system and approach for polymer sequencing as applicable for implementation in connection with one or more example embodiments of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of processes, devices and arrangements for polymer sequencing, and certain aspects have been found to be particularly suited for protein-related and DNA sequencing, such as sequencing approaches involving natural or modified nucleotides or amino acids. While the present invention is not necessarily so limited, various aspects of the invention may be appreciated through a discussion of examples using this context.

According to an example embodiment of the present invention, a polymer is sequenced by analyzing a plurality of such polymers at different stages of assembly. In analyzing the plurality of polymers in steps, certain ones of the polymers are at stages of assembly that are different than other ones of the polymers due, for example, to incomplete synthesis or ineffective cleavage. The polymers are analyzed in a manner that facilitates the identification of a proper stage of assembly for the polymer at a particular step from data including polymers at different stages of assembly.

In one application, the above-discussed approach involves tracking distortion at different stages of assembly of the polymers, and identifying the source of the distortion at each stage. Using the identified source of the tracked distortion, test results characterized by the distortion are processed to mitigate or remove the distortion from the results and thereby facilitate the identification of a polymer sequence that fits the results.

According to another example embodiment of the present invention, a sequencing approach involves the analysis of a polymer such as a protein or DNA via synthesis. A plurality of polymers corresponding to the polymer to be analyzed is synthesized in a step-by-step type of sequencing approach (e.g., such as that used with Pyrosequencing). At each step in the synthesis, the polymers are analyzed in a manner that facilitates the detection and/or determination of a state of the polymers at each step that represents the proper state of the particular polymer.

In another example embodiment of the present invention, a sequencing approach involves the analysis of a polymer via cleavage or other "deconstruction" type approach. A plurality of polymers of the polymer undergoing analysis are cleaved or otherwise deconstructed on a step-by-step basis. At each step, the polymers are analyzed in a manner that facilitates the detection and/or determination of a state of the polymers at each step that represents the proper state of the particular polymer.

In connection with another example embodiment of the present invention, the process of DNA sequencing-by-synthesis and its nonidealities are modeled as a noisy switched linear system parameterized by an unknown DNA sequence, where the switching is performed by the input test sequence. A basecalling problem is then formulated as a parameter detection problem as follows: given a test sequence and its corresponding noisy output sequence, determine the system parameters, i.e., the DNA sequence that minimizes the probability of decoding error. At least one of a maximum likelihood method, maximum a posteriori method, expectation maximization or approximate versions of these methods or similar estimation or detection methods is applied to experimental Pyrosequencing data to generate results having longer read lengths, and in some applications (e.g., with pyrosequencing), read lengths exceeding 200 bases. These generated read lengths, having an order of (e.g., natural or modified) nucleotide bases in a DNA molecule, can be used to determine the sequence and or structure of proteins encoded by that DNA as well as simply to infer the DNA sequence itself. In certain applications, the results are used to provide bounds on the probability of correctly decoding a given sequence.

According to another example embodiment of the present invention, a polymer sequence is determined using a pyrosequencing approach with a noisy switched linear system model as discussed above. The model assumes incomplete incorporation, and includes read noise and non-specific incorporation due to chemical and/or detector non-idealities. These non-idealities may also be referred to as de-phasing, de-synchrony, carry-forward, lag or other related terms. The stochastic nature of the incorporation rate is ignored (but can be included for a more precise fit), and its mean value $p \in (0, 1)$ is considered (which is defined as the average fraction of template strands that incorporate the added base, when incorporation should ideally occur). It should be noted that this is just one embodiment of many models that can be used with similar approaches; in various embodiments, other models that capture the impact and/or behavior of non-idealities in the polymer chemistry of interest are similarly used.

For general information regarding sequencing, and for specific information regarding approaches to sequencing that may be used in connection with one or more example embodiments herein, reference may be made to H. Eltoukhy and A. El Gamal, *Modeling and Base-calling for DNA Sequencing-by-synthesis*, 2006 IEEE International Conference on Acoustics, Speech and Signal Processing, 2006, Volume: 2, pages: II-II (2006), which is fully incorporated herein by reference.

Incomplete incorporation gives rise to a population of template strands with subgroups classified by a representative lag from the ideal subgroup. The process of subgroup formation and evolution can be represented, for example, by a weighted directed acyclic graph such as the example illustrated in FIG. 4 of the above-referenced publication "Modeling and Base-calling for DNA Sequencing-by-synthesis." Nodes, which represent subgroups, are organized in levels each corresponding to a given test. When incorporation occurs, a fraction p of the strands in a subgroup advances to the succeeding subgroup, while a fraction 1−p remains. When no incorporation occurs, the subgroup position remains unchanged, i.e., does not advance to the right, and a weight of 1 is assigned to the corresponding edge. The initial population of template strands becomes distributed over many different subgroups, with laggard subgroups contributing to the overall signal at each test thereby distorting signal quality at longer reads. These distortions are addressed in connection with various example embodiments, with a model as described below; for various definitions and/or explanations of terms as applicable to the model, reference may be made to the aforesaid publication entitled "Modeling and Base-calling for DNA Sequencing-by-synthesis."

In connection with the model, the $i^{th}$ component of the weight vector at time n can be expressed as $$w_{n,i} = a_{i-1,n} w_{n-1,i-1} + (1 - a_{i,n}) w_{n-1,i},$$

where $$a_{i,j} = pI((S^T t_j)_i), (S^T t_j)_i$$

refers to the $i^{th}$ element in the vector $S^T t_j$, and $I(a)=1$ if $a>0$ and zero, otherwise. Thus, the evolution of the weight vector can be described by the switched linear relation $$w_n = A_{t_n} w_{n-1}, \text{ for } 1 \leq n \leq N,$$

where the state-transition matrix $$A_{t_n} = \begin{bmatrix} 1 - a_{1,n} & 0 & \cdots & 0 \\ a_{1,n} & 1 - a_{2,n} & \cdots & 0 \\ 0 & a_{2,n} & \cdots & 0 \\ \vdots & \vdots & \ddots & \vdots \\ 0 & 0 & \cdots & 1 - a_{M+1,n} \end{bmatrix}.$$

Hence, each test vector $t_n$ selects (or switches to) the appropriate state-transition matrix $A_{t_n}$ for the current test.

The noiseless output $x_n$ is defined to be the sum of the contributions from each subgroup of the template population that "tests positive" in response to test $t_n$, i.e., $$x_n = p[Sw_{n-1}]^T t_n.$$

Each term in the inner product of $S^T t_n$ and $w_n - 1$ represents a contribution from a subgroup. To include read noise, the noise is assumed as additive White Gaussian Noise (WGN) that is independent of the signal and system parameters. With noise added, the output of the system is given by $$y_n = x_n + v_n, \text{ for } 1 \leq n \leq N,$$

where $$v_n, 1 \leq n \leq N$$

are independent, identically distributed $\mathcal{N}(0, \sigma^2)$ random variables.

In connection with the above examples, one embodiment involves addressing noise involves by effectively (nearly) canceling system noise by consolidating information from a single analysis run. For instance, noise can be approximated by averaging error values obtained from experimental data, less a model fit.

FIG. 1 shows an overall system 100 (e.g., model) with processing components 110, 120, 130 and 140, in connection with an example embodiment, where the input $t_n$ dictates the evolution of the system with parameters S and p. The system 100 may be implemented using one or more types of devices and corresponding logic. For instance, a sequencing-by-synthesis device (110) can be operated in connection with corresponding logic (120, 130, 140) implemented using a device such as a computer processor executing instructions, a processor-readable storage medium configured with processor executable instructions, a dedicated processor or a programmable logic device; moreover, the sequencing-by-synthesis device and corresponding logic may be implemented together on such a device.

If non-specific incorporation is non-negligibly present, it is modeled by introducing a non-specific incorporation rate, $$0 \leq \epsilon \leq 1$$

akin to the incorporation rate, p. Depending on the outcome of each test, subgroups either advance to the succeeding subgroup with weight p upon success or with weight s upon failure. Since s is typically small (e.g., less than about 0.05), as a good approximation and to simplify the analysis, one subgroup advancement is considered per test. However, a more precise treatment of non-specific incorporation is included in certain embodiments with polymer or sequencing-by-synthesis chemistries involving a significant non-ideality. Where appropriate, data regarding these subgroups is recorded for the modeling.

To include the effect of non-specific incorporation, $a_{i,j}$ is replaced in the definition of $A_{t_n}$ by $$\tilde{a}_{i,j} = I_p((S^T t_j)_i),$$

where $$I_p(s) = p \text{ if } s > 0$$

and $\epsilon$, otherwise.

In connection with the above results, an approach to basecalling is implemented as follows: Given T, p, and $y_1, y_2, \ldots, y_N$, the sequence matrix S is estimated. The problem is cast as a parameter detection problem, using maximum-likelihood detection (MLD) to obtain $$S^* = \underset{S}{\mathrm{argmax}} f(y_1, \ldots, y_N \mid S, T, p)$$

$$= \underset{S}{\mathrm{argmax}} \sum_{n=1}^{N} (y_n - p[Sw_{n-1}]^T t_n)^2.$$

Each homopolymeric region is viewed as producing a particular "channel" pulse in response to a given set of tests over time. Accordingly, each $x_n$ is decomposed into the sum of the shifted pulse responses due to each individual homopolymeric region as $$[x_1 x_2 \ldots x_N]^T = H_T [1 1 1 \ldots 1 1 1]^T,$$

where $$H_T = p \cdot \begin{bmatrix} b_{1,1} & 0 & \cdots & 0 \\ b_{2,1} & b_{2,2} & \cdots & 0 \\ \vdots & \vdots & \cdots & \vdots \\ b_{N,1} & b_{N,2} & \cdots & b_{N,M} \end{bmatrix},$$

and $$b_{i,j} = w_{i-1,j} (S^T t_i)_j.$$

Each column of $H_T$ represents the contribution from an individual homopolymeric region to the resultant $x_1, x_2, \ldots, x_N$.

Figure 2A:
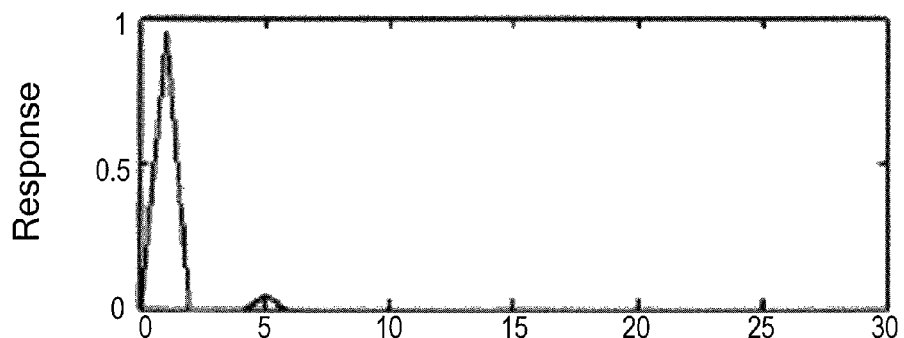
FIG. 2 shows plots of a pulse response as a function of the number of tests respectively in 2A, 2B and 2C.
Figure 2B:
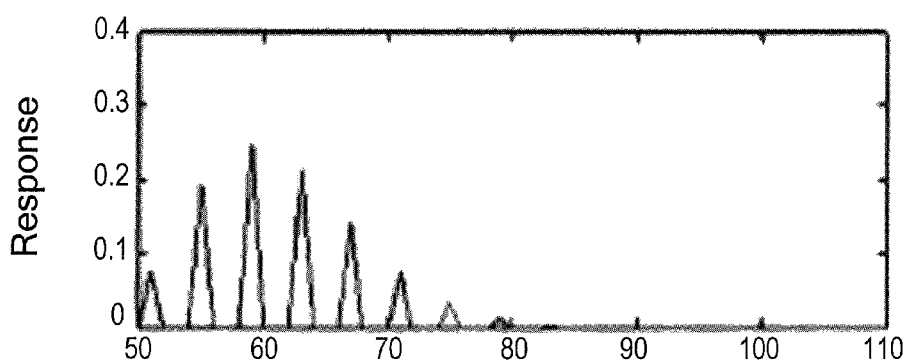
Figure 2C:
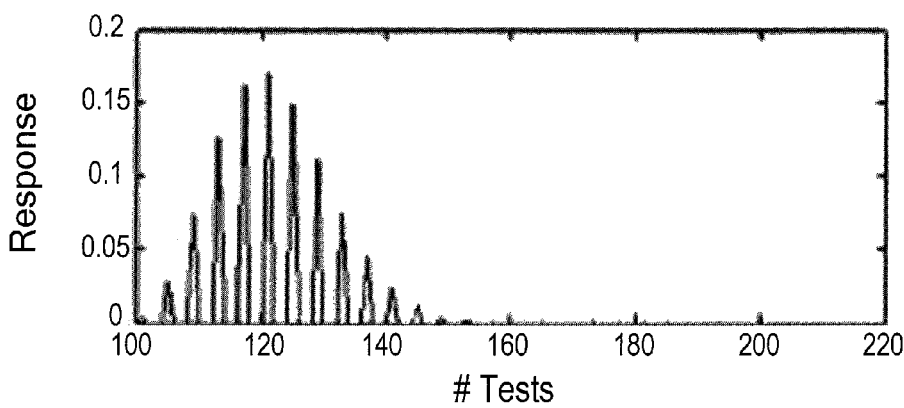

FIG. 2 shows plots of a pulse response as a function of the number of tests respectively in 2A, 2B and 2C. Note that as long as p<1, each homopolymeric region contributes to succeeding outputs even for very large N, although possibly negligibly, or in communication theory parlance, the channel exhibits severe intersymbol-interference (ISI).

Two features of the model discussed above are selectively exploited to reduce the computational complexity of basecalling; first, a limited portion of the puke response is used as significant, and second, tests of different base types are reasonably uncorrelated for values of p that are close to one. Taking these properties into consideration, the soft-input Viterbi algorithm (VA, see, e.g., G. D. Forney, "The Viterbi algorithm," *Proc. IEEE,* vol. 61, N. 3, pp. 268-278, March 1973) is modified to perform base-calling and, hence, approximate maximum-likelihood sequence detection (MLSD).

Four trellises are used (each one with states corresponding to only one test type), and symbol-by-symbol detection is performed to obtain a rough estimate of the sequence to initialize the algorithm. A standard VA is performed on each of the four trellises, with the best surviving paths from the other three trellises filling in the gaps. The paths are extended one path length at a time, and the trellises are iterated through based on the order specified by the test matrix T. In this manner, MLSD is approximated using an iterative, partial-MLSD approach. In some applications, a confidence score is generated for each base using a soft-output VA (SOVA) or List VA (LVA). For example SOVA approaches that may be implemented in connection with various example embodiments, reference may be made to J. Hagenauer, P. Hoeher, "A Viterbi Algorithm With Soft Decision Outputs and Its Applications," *Proceedings of IEEE GLOBECOM*, pp. 47.1.1-47.1.6., November 1989. For example LVA approaches that may be implemented in connection with various example embodiments, reference may be made to N. Seshadri, C-E. W. Sundberg, "List Viterbi Decoding Algorithms with Applications," *IEEE Transactions on Communications*, vol. 42, no. 2/3/4, pp. 313-323, 1994.

Figure 3:
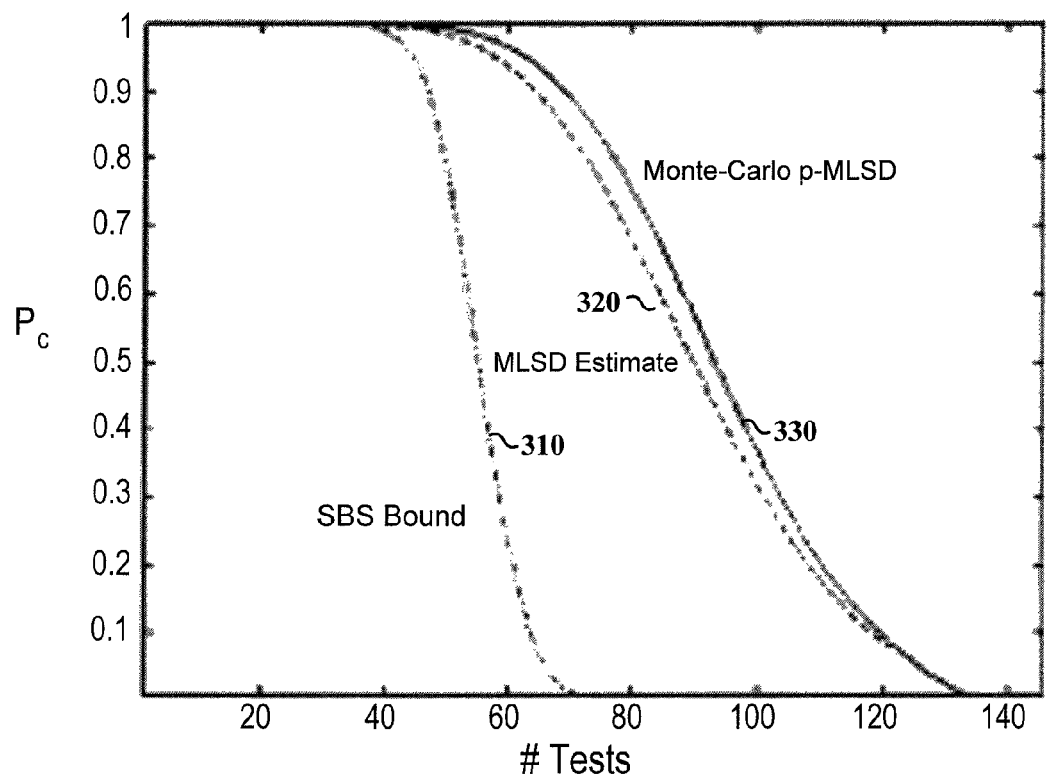
FIG. 3 shows plots of pulse responses as a function of a number of tests in sequencing, according to another example embodiment of the present invention.

In some applications, the above communication analogy is used to derive bounds and estimates on the probability of correct decoding ($P_c$). For example, FIG. 3 shows a plot 310 of the lower bound on Pc obtained assuming symbol-by-symbol (SBS) detection (i.e., with no lookahead) and a plot 320 of a conservative estimate assuming MLSD with worst case ISI to $P_c$ obtained using a Monte-Carlo simulation of the partial-MLSD algorithm (plot 330).

Figure 4:
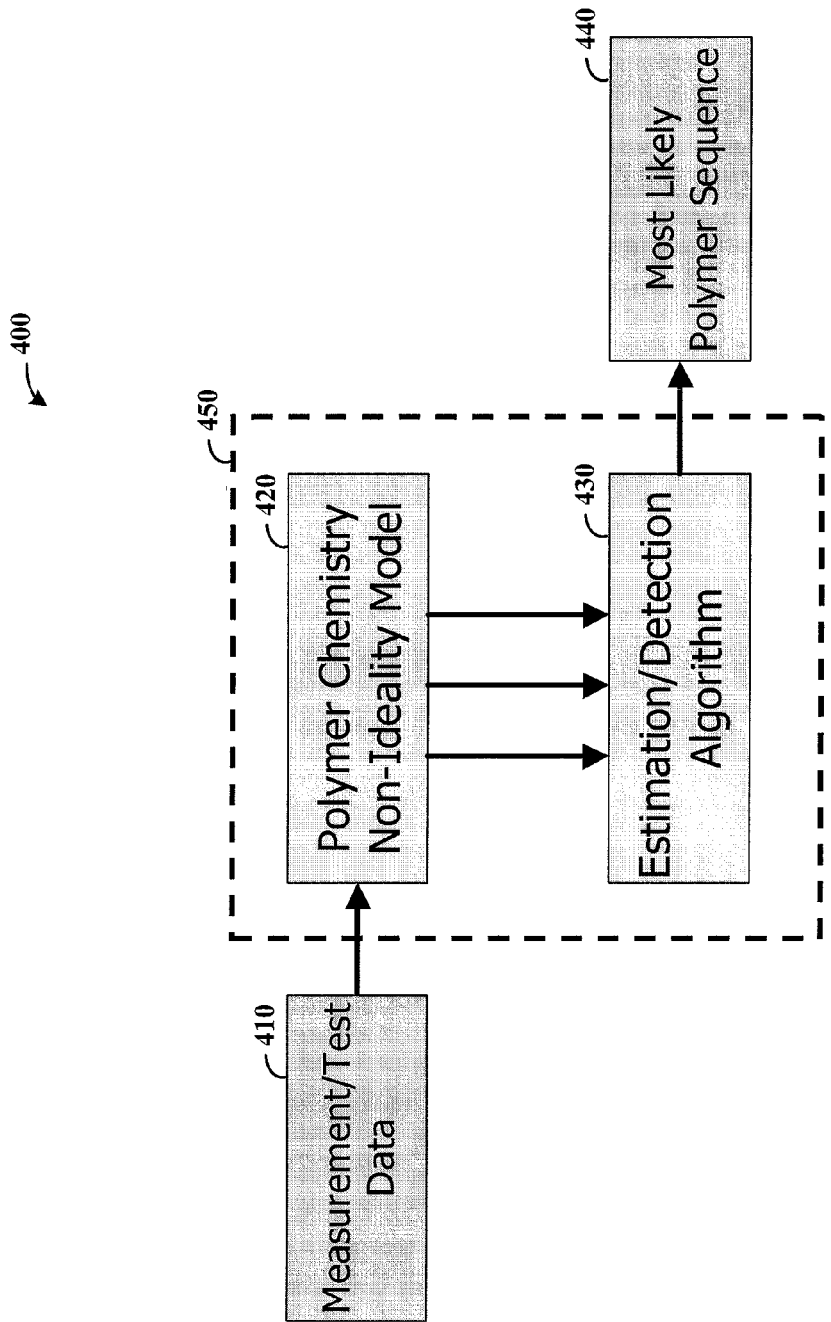
FIG. 4 is a data flow diagram for an approach to sequencing, according to another example embodiment of the present invention.

FIG. 4 is a data flow diagram and approach 400 for an approach to sequencing, according to another example embodiment of the present invention. The arrangement and approach 400 may be implemented, for example, in connection with one or more of the example embodiments described above, such as that shown in FIG. 1 and otherwise. Measurement/test data 410 is provided to a sequencing processor 450. A non-ideality model function 420 is implemented to model underlying chemistry and noise in the data 410 using one or more of a variety of approaches. For instance, individual polymer subgroups can be tracked together with their contribution to the test data.

The modeled chemistry and noise is processed at an estimation/detection algorithm function 430, using the model data to choose a maximum likely, or a posteriori, sequence that best corresponds to the measurement/test data 410. The estimation/detection algorithm function 430 then outputs a most likely polymer sequence 440.

The approaches to sequencing discussed herein are applicable to a variety of polymers in a variety of manners. The following example describes such applications. In one application, preprocessing steps are taken before applying the iterative partial-MLSD algorithm to experimental Pyrosequencing data. A baseline correction is performed due to the changing chemical background signal present as well as integration of the total photoemission from each test. The integrated signals are normalized to account for chemical variations from run to run. The scaling factor for such normalization is automatically extracted from the histogram of the photoemission values. Additionally, the parameters of the model are estimated, e.g., p, base specific gains, and others. These parameters are similarly extracted from a subset of the data itself through an iterative fitting procedure or can be extracted from a portion of the sequence that is known a priori. The iterative partial-MLSD algorithm is applied to Pyrosequencing datasets.

A multitude of dataset ranges are used in connection with various example embodiments. In one implementation, the datasets range in length between 55 and 224 bases, with the first 170 out of 208 and 205 out of 224 bases of the longest two templates, as well as all shorter sequences, correctly decoded. In another implementation, pyrosequencing systems are used in conjunction with a base-calling approach discussed above to read lengths of between about 200-300 bases or more.

Various example embodiments are implemented in connection with the approaches discussed hereinbelow, generally describing a communication framework for polymer sequencing.

In this discussion, we develop an algorithm for enhanced automated base-calling in DNA sequencing-by-synthesis-based approaches predicated on a communication-theoretic framework. Although we focus on Pyrosequencing specifically, the analytical model and resulting decoding algorithms are suitable for a variety of sequencing-by-synthesis methods. The basis of the analysis is a chemically defined "communication-channel" model. The model is similar to an Additive White Gaussian Noise (AWGN) channel with severe intersymbol interference, except that the system impulse response is a function of the input signal. This communication theoretic approach to modeling Pyrosequencing makes it possible to leverage the vast body of work on detection to develop accurate base-calling algorithms. We use this framework, both to perform decoding of the received signal set as well as to derive bounds on the probability of decoding error.

The rest of the discussion is organized as follows. In the next section we give a general description of the Pyrosequencing chemistry and the non-idealities that limits its read length. In Section III, we develop a model of the underlying chemistry. In Section IV, we discuss the similarities between this model and the AWGN channel with intersymbol interference. In Section V, we explore both symbol-by-symbol (SBS) and approximate maximum-likelihood (ML) sequence detection algorithms for base-calling. In Section VI, we detail the performance of both SBSD and MLSD in terms of probability of error versus read length. Finally, in Section VII, we present experimental data highlighting the performance of the approximate MLSD algorithm.

II. Background

First, we familiarize the reader with some of the biological terms that will be used throughout the discussion. Deoxyribonucleic acid or DNA is a polymer or strand composed of only four possible constituent molecules or nucleotide bases; these bases are adenine (A), cytosine (C), guanine (G), and thymine (T). Moreover, a DNA strand can be either single or double-stranded. Single-stranded DNA (ssDNA) can bind with its unique ssDNA complement to form a double-stranded version of itself (dsDNA), whereby A bases bond only with T bases and C bases bond only with G bases. For example, the sequence ACTGGC is complementary to TGACCG. The goal of DNA sequencing in general is to "read" a particular ssDNA strand or template, that is, to reliably determine the sequence of its bases, since these bases can appear in any order. As DNA sequences can be several hundred millions of bases in length, it is the goal of any de novo DNA sequencing approach to have as long and as accurate of a read length as possible to aid in DNA assembly, a process by which short DNA reads are pieced together to form the entire sequence. The terms nucleotide and base will be used interchangeably throughout this discussion to refer to a nucleotide base. In addition, the term homopolymeric refers to sequences or portions thereof composed of a single base type. We next describe the Pyrosequencing chemistry and its non-idealities in order to provide the reader with better physical intuition regarding the model presented herein for DNA sequencing-by-synthesis.

A. Pyrosequencing

Figure 5:
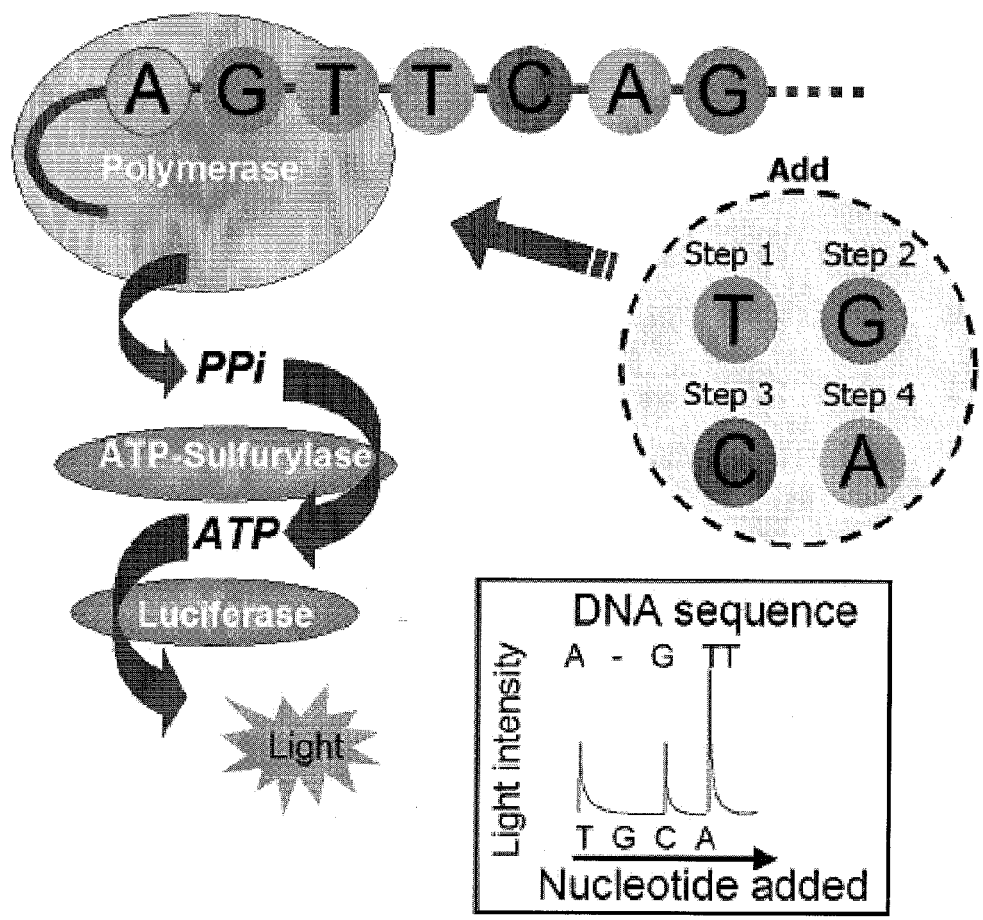
FIG. 5 illustrates a DNA template undergoing Pyrosequencing reaction with the output signal is shown in the inset box, consistent with embodiments of the present disclosure.

Pyrosequencing is a DNA sequencing-by-synthesis method by which an ssDNA is sequenced through an iterative buildup of its complement, the progress of which is inferred through detection of the resultant chemical photoemission. The chemistry itself consists of a mixture of 4 main components: the ssDNA template (strand to be sequenced), polymerase to accelerate the rate of nucleotide incorporation, ATP-sulfurylase to help convert pyrophosphate (PPi) into ATP, and luciferase (firefly enzyme) to indirectly quantify the ATP in solution via light emission. Since each nucleotide incorporation event results in the release of one PPi molecule, this release can be detected via the enzymatic cascade precipitated by ATP-sulfurylase and luciferase as the eventual emission of a proportional number of photons. Typically, a template is sequenced by repeatedly cycling through the addition/dispensation of the 4 possible bases, A, C, G, T, with the resulting incorporation quantified at each step through the detection of the number of photons emitted. The one twist is that the incorporation stops only at the first base not equal to the current one, i.e., each homopolymeric region is sequenced at a time. FIG. 5 illustrates this process for the DNA template AGTTCAG. Ideally, a light signal linearly proportional to the number of bases complementary to that added at the current position is detected. Assuming a dispensation order of T, G, C, A, we obtain a signal proportional to the run-length code, 1T-0G-1C-2A, and can infer that the first four bases of the template sequence is AGTT. In this way, there is a direct relationship between a template and its Pyrogram, i.e., the plot of a template's detected light signal versus nucleotide dispensation, from which the sequence of the template can be easily inferred. This overall scheme to DNA sequencing is analogous to the serial readout approach employed by a cassette player, whereby the single-sided DNA molecule is similar to the tape and the polymerase enzyme represents the tape head.

B. Non-Idealities

The above description details the ideal outcome of the Pyrosequencing chemistry, whereby the length of the DNA template to be sequenced can be arbitrarily long. Current approaches to Pyrosequencing, however, can only sequence up to 40 bases reliably, due to the existence of several non-idealities in the reading process. In practice, there are three main sources of signal degradation, in addition to overall system noise, that limit realizable read lengths: incomplete incorporation, misincorporation/contaminated additions, and product inhibition/secondary structure interactions.

Incomplete incorporation is the main non-ideality responsible for the degradation in read lengths. It is predicated on the concept that the polymerase-assisted incorporation reaction itself, $$DNA_n + dNTP \xrightarrow{polymerase} DNA_{n+1} + PPi,$$

Figure 6:
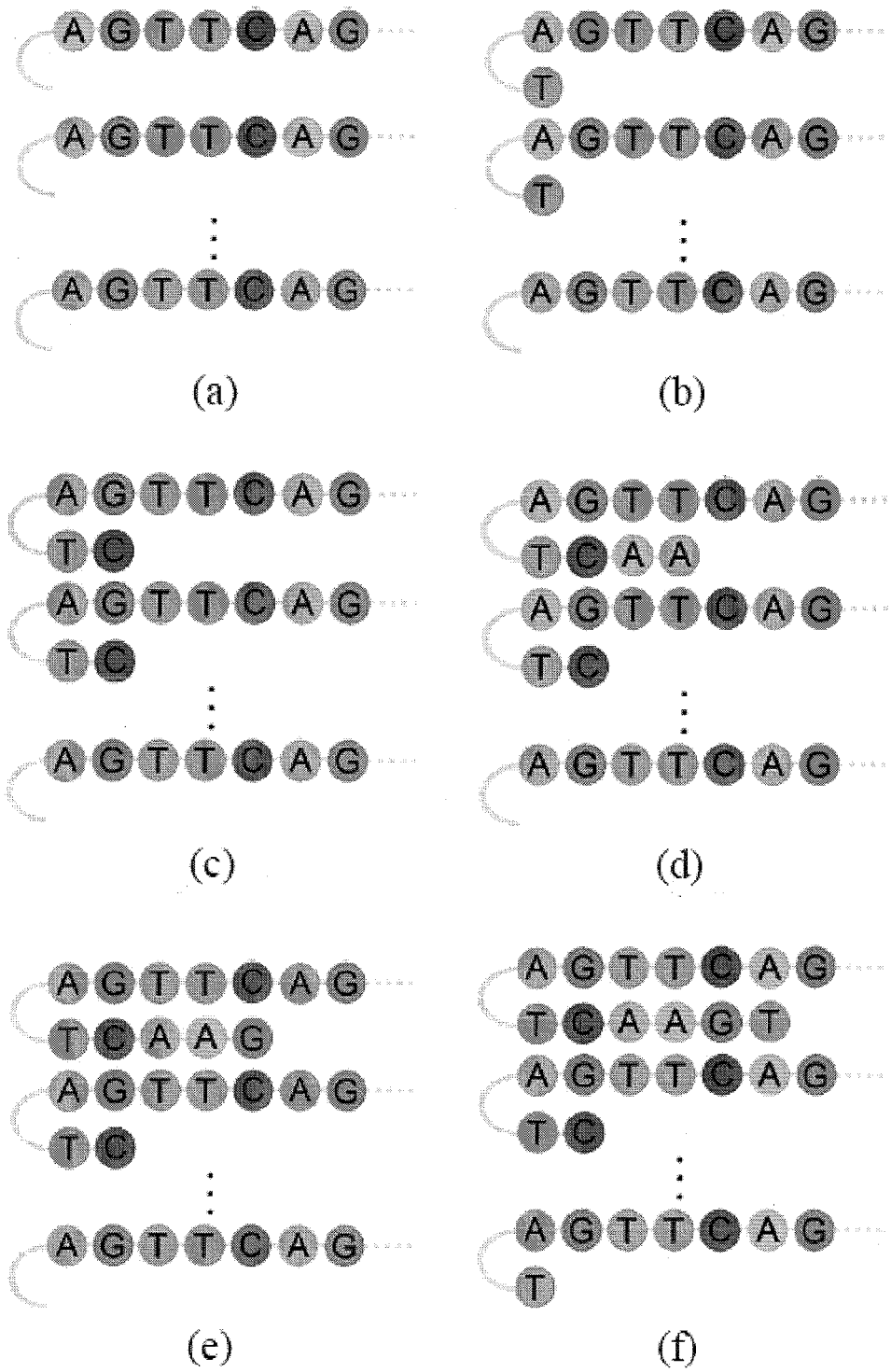
FIG. 6(a) illustrates incomplete incorporation phenomenon relative to the starting state of the DNA strand population, consistent with embodiments of the present disclosure.
FIG. 6(b) illustrates where the base T is added, consistent with embodiments of the present disclosure.
FIG. 6(c) illustrates where the base C is added, consistent with embodiments of the present disclosure.
FIG. 6(d) illustrates where the base A is added, consistent with embodiments of the present disclosure.
FIG. 6(e) illustrates where the base G is added, consistent with embodiments of the present disclosure.
FIG. 6(f) illustrates where the base T is added again resulting in an incorporation event occurring at two different positions in the sequence, consistent with embodiments of the present disclosure.

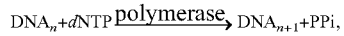

where dNTP refers to a single nucleotide, is a stochastic process with a mean forward and reverse rate. As such, given that we are forced to sequence multiple copies of the template to amplify the signal, the number of strands that incorporate the dispensed nucleotide follow a Poisson distribution with a rate determined by the overall forward and reverse reaction rates. The stochastic nature of the process implies that not all template molecules incorporate when they ideally should and herein lies the crux of this most significant non-ideality. In short, a synchronization problem occurs, where by continued analogy with cassette tape reading, instead of using one tape head, we have many tape heads with slightly varying read rates, and only the sum of their signals is observed. FIG. 6 illustrates the problem showing snapshots of the representative template strands versus nucleotide dispensation. In FIG. 6(a), at the start of sequencing, all strands are synchronized with one another. In FIG. 6(b), the nucleotide T is added; however, we now have two representative subgroups, those that incorporated the T base and those that failed to do so. Sequencing proceeds normally until when in FIG. 6(d), another subgroup is generated, that is, those that failed to incorporate the added A base. Finally, FIG. 6(f) shows incorporation at two sites, the "ideal" zero-lag subgroup and at a previous incorporation position on a laggard subgroup. The problem is of course that both of these subgroups contribute to the output signal. In this way, this arising convoluted signal distorts the output and complicates the decoding of the Pyrogram to recover its representative underlying sequence. It is important to note that the extraneous subgroups generated by incomplete incorporation are all lagging in nature, since a strand only incorporates correctly or does not.

Spurious leading subgroups, which can only be engendered by undesired nucleotide additions, are more of a second-order non-ideality and are caused by misincorporation as well as contaminated dispensations. Misincorporation is due to the fact that polymerase has a non-zero probability (very small, i.e., 1 in $10^3$-$10^4$) of incorporating the wrong nucleotide. The problem with this of course is that it counts as a valid incorporation event and advances the polymerase to the next position on the template. Contaminated dispensations, on the other hand, occur when the nucleotide dispensed is contaminated with dilute concentrations of some or all of the other three nucleotides. This contamination is generally on the order of 0.01%, once again a typically negligible level.

The third major class of non-idealities is due to product inhibition and secondary structure interactions of the template molecules. Product inhibition refers to the phenomenon whereby the accumulation of chemical byproducts inhibits the forward reactions from proceeding. Fortunately, a clever combination of chemistry and engineering can be used to combat this non-ideality, such as, employing reaction chambers that confine only the template, while continually flushing out accumulated products. The other non-ideality that occurs in practice is the effect of secondary-structure interactions in the template. This can cause a fluctuation of the incorporation rate at certain stretches where hairpin structures may exist. This too can be ameliorated through the introduction of additional enzymes to decrease the likelihood of such interactions.

In addition to the above three non-idealities, there is also system noise due to chemical variations arising from fluctuating nucleotide dispensations and mixing efficiency, as well as measurement noise due to the photosensing device.

For the rest of the discussion, we will concern ourselves only with incomplete incorporation and system noise, since these constitute the dominant distortion phenomena encountered using Pyrosequencing. Fortunately, extension of the framework to include other non-idealities is relatively straightforward.

III. Sequencing-by-Synthesis Model

Figure 7:
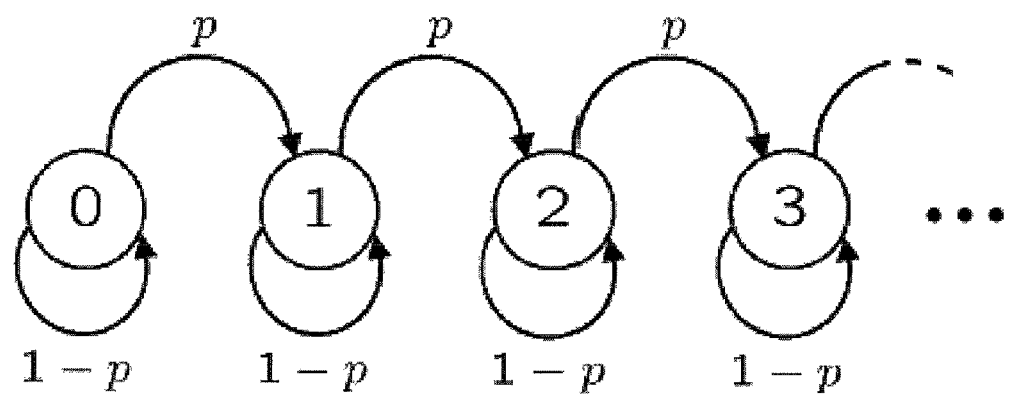
FIG. 7 illustrates a Markov chain depicting simplified model of single strand nucleotide incorporation, consistent with embodiments of the present disclosure.

To model incomplete incorporation, we first make some simplifying assumptions, which are well substantiated by empirical data. First, we ignore the stochastic nature of the incorporation rate, and only consider its mean value $p \in (0, 1)$, which represents the average fraction of template strands that incorporate the dispensed nucleotide, when incorporation should ideally occur. For example, p=1 implies that no incomplete incorporation phenomenon exists and consequently no distortion occurs. To illustrate why use of a deterministic value for p is reasonable, consider a hypothetical solution consisting of a single strand with only one base type. When we add the complementary base, incorporation occurs with probability p and does not occur with probability 1−p (see FIG. 7, Markov chain depicting simplified model of single strand nucleotide incorporation.) Assuming the outcomes of the tests to be independent, at the end of N incorporation tests, the probability of ending up at a certain base position k is given by the binomial probability law, i.e., $$P_N(k) = \binom{N}{k} p^k (1-p)^{N-k}$$

Now consider Z strands with independent and identically distributed incorporations. The number of strands $Z_n$ terminating at each position n, for $0 \le n \le N$, follows a multinomial probability law $$Q_N(Z_0 = z_0, Z_1 = z_1, \ldots, Z_N = z_N) = \frac{Z!}{\prod_{n=0}^{N} z_n!} \prod_{n=0}^{N} \theta_n^{z_n},$$

where $$\theta_n = P_N(n) \text{ and } \sum_{n=0}^{N} z_n = Z.$$

The mean and variance of $Z_n$ are given by $$E(Z_n) = Z P_N(n) \text{ and}$$

$$\sigma_{Z_n}^2 = Z P_N(n)(1 - P_N(n))$$

As $$Z \to \infty, \frac{\sigma_{Z_n}}{Z} \to 0 \text{ as } \sqrt{Z}.$$

Since in practice $Z > 10^6$, the standard deviation is very small and this suggests we are justified in assuming that a deterministic fraction p transition to the succeeding state.

Furthermore, we also assume that p can be empirically determined and is slowly varying, hence constant throughout long stretches of DNA sequencing.

Figure 8:
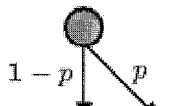
FIG. 8 illustrates a directed acyclic graph (DAG) showing state distribution of DNA template (TAG) population versus added base where the corresponding fraction of the initial strand population at each node is highlighted in the table and are denoted as subgroup weights, consistent with embodiments of the present disclosure.

It is clear from the above discussion, that incomplete incorporation gives rise to a population of template strands with subgroups classified by a representative lag from the ideal subgroup. It is also clear, given the discrete nature of DNA (in terms of constituent bases), that given a strand of M homopolymeric regions, we can have at most M+1 subgroups once sequencing has concluded. This process of subgroup formation and evolution can be represented by a weighted directed acyclic graph as illustrated in FIG. 8. The nodes, which represent the subgroups, are organized in levels each corresponding to a base addition step. The edges and their weights capture the evolution of the subgroups in response to each base addition step. When incorporation occurs, a fraction p of the strands in a subgroup advance to the succeeding subgroup, while a fraction 1−p remains. Hence a weight of p is assigned to the edge from the parent node corresponding to the subgroup to its child on the right and a weight of 1−p is assigned to its other child. When no incorporation occurs, the subgroup position remains unchanged, i.e., does not advance to the right, and a weight of 1 is assigned to the corresponding edge. The number of non-zero subgroups or nodes at a given level of the graph grows at most linearly with the number of levels, since branch recombination occurs except for the leading subgroup. From FIG. 8 the reason for the eventual severe distortion in signal quality becomes apparent. The initial population of template strands becomes distributed over many different subgroups, with laggard subgroups contributing to the overall signal at each nucleotide dispensation.

Before describing our model, we introduce the following needed definitions. First we assign to each homopolymeric region of length $l \in \{1, 2, \ldots, K\}$, in the template DNA strand, a "run-length" codeword as follows:

AA . . . A ↔ (1000)
CC . . . C ↔ (0100)
GG . . . G ↔ (0010)
TT . . . T ↔ (0001)

Although, in general, there is no bound on l, we limit l to a maximum of K to simplify the analysis. Moreover, larger values of l occur with much lower probabilities in naturally occurring DNA sequences. We then form the 4×(M+1) DNA sequence matrix S whose columns are the codewords corresponding to the M homopolymeric regions of the given template DNA strand with the (M+1)th column all zeros. For example, the oligonucleotide, TAGCGG, is represented by, $$S = \begin{bmatrix} 0 & 1 & 0 & 0 & 0 & 0 \\ 0 & 0 & 0 & 1 & 0 & 0 \\ 0 & 0 & 1 & 0 & 2 & 0 \\ 1 & 0 & 0 & 0 & 0 & 0 \end{bmatrix}$$

Note that at each iteration, a certain nucleotide is dispensed. Alternatively, we can think of each nucleotide dispensation as a "test," which aims at detecting the presence of a certain nucleotide at the current position of the template. Thus, an "A test," for example, attempts to detect the presence of the base A at the current position in the sequence. In this way we sidestep the details regarding DNA complementariness and hence this is the terminology we employ for the remainder of the discussion. Although in practice a cyclical testing order is used, i.e., ACGTACGT . . . , for generality, we allow for any testing sequence. To indicate which test is performed at each step, we define the DNA test sequence vector t of length N such that $t_n=1$ if test n is for base A, 2 if for base C, 3 if for base G, and 4 if for base T. For example, the test sequence for TGCATG, is represented by t=[4 3 2 1 4 3].

Next, we define the incorporation vector u of length N as a row vector whose nth element $u_n$ is the ideal number of incorporated bases due to test $t_n$ (i.e., when p=1). For example, for the DNA template in FIG. 8, u=[100101]. As we will show soon, u is a function of S and t.

Finally, for each test $1 \le n \le N$, we define the column weight vector $w_n$ of length M+1 to consist of the fractions of the total template population in each possible subgroup after the nth test, beginning with $w_0 = [1\ 0\ 0\ \ldots\ 0]^T$. Thus, by definition, for each n, $w_{n,i} \ge 0$, for all i, and $\Sigma_i w_{n,i}=1$. For the example DNA template sequence in FIG. 8, the weight vectors are the rows of subgroup weights, i.e., $w_1=[1-p\, p\, 0\, 0]^T, \ldots, w_4=[1-p\, p(1-p)\, p^2\, 0]^T$.

Now that we have defined the necessary variables and parameters, we can relate them to the observed output at time n, i.e., after the nth test.

From the above discussion, it can be seen that the ith component of the weight vector at time n can be expressed in the recursive form $$w_{n,i} = a_{i-1,n} w_{n-1,i-1} + (1-a_{i,n}) w_{n-1,i},$$

Where $a_{i,j}=pI(s_{t_j,i})$, $s_{t_j,i}$ refers to the ith element in the $t_j$th row of S, and $I(a)=1$ if $a>0$ and zero, otherwise. For example, the second subgroup weight in $w_5$ for the template in FIG. 8 is given by $$w_{5,2} = \alpha_{1,5} w_{4,1} + (1-a_{2,5}) w_{4,2}$$
$$= p(1-p) + (1-0)(p(1-p))$$
$$= 2p(1-p).$$

Combining these recursive equations, we can describe the evolution of the weight vector in the following state-space form $$w_n = A_n w_{n-1}, \text{ for } 1 \leq n \leq N, \quad (1)$$

where the state-transition matrix $$A_n = \begin{bmatrix} 1-a_{1,n} & 0 & \ldots & 0 \\ a_{1,n} & 1-a_{2,n} & \ldots & 0 \\ 0 & a_{2,n} & \ldots & 0 \\ \vdots & \vdots & \ddots & \vdots \\ 0 & 0 & \ldots & 1-a_{M+1,n} \end{bmatrix}.$$

Now, we define the noiseless output $x_n$ as the sum of the contributions from each subgroup of the template population that "tests positive" in response to test tn, i.e., $$x_n = p s_{t_n} w_{n-1}, \quad (2)$$

where $s_{t_n}$ is the $t_n$th row of the S matrix defined above. Each term in the inner product of $s_{t_n}$ and $w_{n-1}$ represents a contribution from a subgroup.

Since $x_n$ is a function of $w_n$, it can be thought of as the output of a linear time varying system described in the state-space form, where $w_n$ is the state of the system at time n.

We can find an explicit formula for the output v as follows. First, by repeated back-substitution of the state-space equation (1), we obtain $$x_n = p s_{t_n} \left( \prod_{i=1}^{n-1} A_i \right) w_0.$$

By careful examination of the form of each term in the above inner product, it can be shown that for a cyclical testing order $$x_n = \sum_{i=0}^{r(u_1^n,t_n)-1} \left[ \binom{j+i-1}{i} p^j (1-p)^i \cdot s_{t_n,j} \right],$$

where $$u_1^n \triangleq [u_1 u_2 \ldots u_n], \; j = m - q(u_1^n, n-4i), \; q(u_1^n, n-4i)$$

is the number of non-zero entries in $u_1^n$ with index great than $n-4i$, $m=q(u_1^{n-1},0)+1$, and $r(u_1^n,t_n)$ is the number of non-zero values in $u_1^n$ corresponding to test $t_n$. Note also that u is a function of S and t, since $$u_n = s_{t_n,m},$$

where again $$m = q(u_1^{n-1}, 0) + 1.$$

From this explicit relation for $x_n$, it becomes apparent that each output is simply a sum of a subset of the terms in a modified binomial expansion. As an example, for the case where $t=[1\,2\,3\,4\,1\,2\,3\,\ldots]$ and for DNA sequence, ACGTACGT..., the above relation reduces to $$x_n = \sum_{i=0}^{\lfloor (n-1)/4 \rfloor} \binom{n-3i-1}{i} p^{n-4i} (1-p)^i. \quad (3)$$

Figure 9:
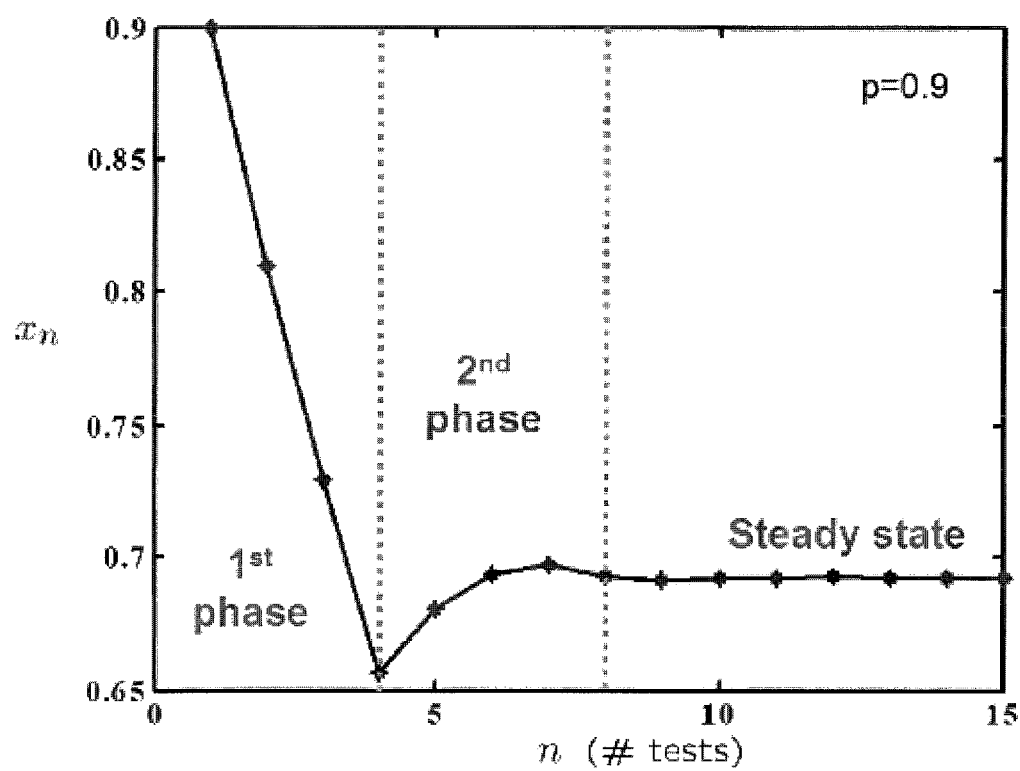
FIG. 9 illustrates an output signal versus the number of tests n, for the example case of template, ACGTACGT . . . and t=[1 2 3 4 1 2 3 4 . . . ], consistent with embodiments of the present disclosure.

FIG. 9 plots equation (3) versus the number of tests n, for p=0.9. As can be seen, the output for this example has three main phases (i) a simple multiplicative decay where there are no contributions from lagging subgroups, (ii) a multiplicative decay plus one contribution from lagging subgroups, and (iii) a steady-state where the decline in signal from the leading subgroups is matched by the addition of signal from lagging ones.

FIG. 9 illustrates an output signal versus the number of tests n, for the example case of template, ACGTACGT... and t=[1 2 3 4 1 2 3 4 ...].

Now a reasonable question to ask is, given the sequence $x_1, x_2, \ldots, x_N$, can S be uniquely determined? This is indeed the case. To show this, we rewrite equation (2) as $$x_n = p u_n w_{n-1,m} + p s'_{t_n} w_{n-1},$$

where $m=q(u_n^{n-1},0)+1$ is the position of the ideal subgroup in $w_{n-1}$ after tests $t_1^{n-1}$ and $s'_{t_n}$ represents a row from the partial sequence matrix $S_1^{m-1}$, in which only the first m−1 columns contain non-zero elements. Thus, $x_n$ is the sum of two terms, the contribution from the ideal subgroup after test n and the contribution from lagging groups. By solving for un in the above relation, it can be shown by induction that S can be uniquely determined from $x_1, x_2, \ldots, x_N$, since given $x_1, \ldots, x_n$ for $n \leq N$, $S_1^{m-1}$, $t_1^{n-1}$ and $w_{n-1}$, $$u_n = s_{t_n,m} = \frac{x_n - p s'_{t_n} w_{n-1}}{p w_{n-1,m}}.$$

In other words, to solve for the next base in the sequence, we calculate the signal contribution from preceding bases, subtract that from the observed signal and then normalize the remainder by the size of the ideal subgroup. This implies that we can arbitrarily solve (on an iterative symbol-by-symbol basis) for any read length m given we observe the noiseless output $x_n$ and given infinite precision.

In practice, of course, the output is corrupted by system noise, which is the second major non-ideality we discussed. We model this as additive White Gaussian Noise (WGN) that is independent of the signal and system parameters. With noise added, the output of the system is given by $$y_n = x_n + v_n, \text{ for } 1 \leq n \leq N,$$

where $v_n$, $1 \leq n \leq N$ are independent, identically distributed N $(0, \sigma^2)$ random variables, $$x_n = ps_{t_n} w_{n-1} = pu_n w_{n-1,n} + ps'_{t_n} w_{n-1}$$

and $$w_n = A_n w_{n-1}.$$

IV. Communication Channel Analogy

From the results of the previous section, it is clear that given a DNA sequence and a test vector, we can solve for the expected value of the output signal $E(y_n) = x_n$, at each time n. However, it is the reverse procedure that is of much more practical interest to genomics: Given $y_1, y_2, \ldots, y_N$, how well can we estimate the underlying sequence matrix S? In practice, this type of decoding is generally referred to as base-calling. Thus, we wish to determine the underlying sequence matrix S, given $y_1, y_2, \ldots, y_N$, t, and p. We can employ maximum-likelihood detection (MLD) to derive the solution as follows:

$$\begin{aligned}
S^* &= \underset{S}{\operatorname{argmax}} f(y_1, \ldots, y_N \mid S, t) \\
&= \underset{S}{\operatorname{argmax}} f(y_1, \ldots, y_N \mid u, t) \\
&= \underset{S}{\operatorname{argmax}} f(x_1 + v_1, \ldots, x_N + v_N \mid u, t) \\
&= \underset{S}{\operatorname{argmax}} \prod_{n=1}^{N} f(x_n + v_n \mid u_1^n, t_1^n) \\
&= \underset{S}{\operatorname{argmax}} \sum_{n=1}^{N} \ln f(x_n + v_n \mid u_1^n, t_1^n) \\
&= \underset{S}{\operatorname{argmax}} \sum_{n=1}^{N} \ln \frac{1}{\sqrt{2\pi}\,\sigma} e^{-(y_n - ps_{t_n} w_{n-1})^2 / 2\sigma^2} \\
&= \underset{S}{\operatorname{argmax}} \sum_{n=1}^{N} -(y_n - ps_{t_n} w_{n-1})^2 \\
&= \underset{S}{\operatorname{argmin}} \sum_{n=1}^{N} (y_n - ps_{t_n} w_{n-1})^2.
\end{aligned}$$

Thus, we only need to minimize the $l_2$ distance between the observed sequence and the chosen sequence over the search space of all possible input sequences. However, the computational complexity of this approach is daunting, since given the above constraint of at most K bases in a row, we must search through $4/3(3K)^M$ possible sequences. For M=200 and K=5, this is approximately $2.2 \times 10^{235}$ sequences. Clearly, further insight into the model is necessary in order to reduce the computational complexity.

The above derivation is analogous to the derivation of maximum-likelihood detection (MLD) for the conventional Additive White Gaussian Noise (AWGN) channel, where the ML sequence is the closest sequence in the $l_2$ sense from the received sequence. Indeed, the similarity between this DNA sequencing-by-synthesis model and the AWGN communication channel is an important observation, since it allows us to leverage the vast literature on decoding methods for AWGN communication channel is an important observation, since it allows us to leverage the vast literature on decoding methods for AWGN channel. To further the analogy, we can think of each element of the incorporation vector u as an M-PAM symbol (where here M=K+1) transmitted over an AWGN communication channel with memory represented by our above model of incomplete incorporation. Recall that the noiseless output is given by $$x_n = pu_n w_{n-1,n} + ps'_{t_n} w_{n-1},$$

where the first term represents the contribution from the current transmitted symbol $u_n$ and the second represents the contribution from other subgroups. In other words, a non-negligible intersymbol interference (ISI) phenomenon exists; however, this ISI is more insidious than in the conventional communication channel setting as it is not constant but depends on the underlying sequence.

Figure 10:
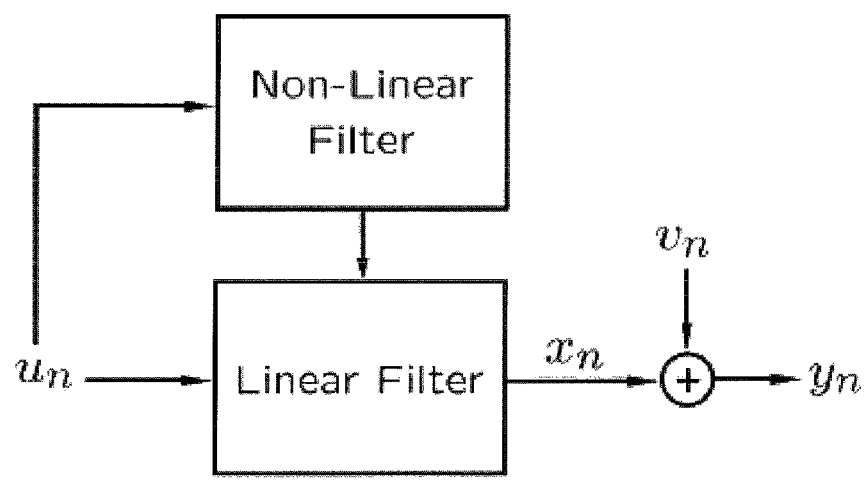
FIG. 10 illustrates a block diagram of AWGN communication channel representation of DNA sequencing-by-synthesis, where the output represents a convolution of the input sequence with the time-varying and signal dependent impulse response, which is non-linearly dependent on the input, consistent with embodiments of the present disclosure.

FIG. 10 shows a block diagram of the equivalent communication channel represented by this biological system. The DNA sequence itself in conjunction with the test vector non-linearly affects the memory in the channel (i.e., the taps of its discrete-time impulse response). By further borrowing from communication theory, it is clear that a causal or a symbol-by-symbol detector is not optimal due to the inherent correlation between received signals. The degree of suboptimality of these methods, however, depends on the severity of the ISI.

Channel Impulse Response

To gain some insight into the severity of the channel ISI, we decompose each $x_n$ into the sum of the scaled impulse responses due to each individual homopolymeric region, since $x_n$ is a linear combination of the incorporation events over the existing subgroups. Mathematically, we decompose the $x_n$ as $$[x_1 x_2 \ldots x_N]^T = H_{u_1^N} [111 \ldots 111]^T,$$

where $$H_{u_1^N} = p \cdot \begin{bmatrix} b_{1,1} & 0 & \ldots & 0 \\ b_{2,1} & b_{2,2} & \ldots & 0 \\ \vdots & \vdots & \ldots & \vdots \\ b_{N,1} & b_{N,2} & \ldots & b_{N,M} \end{bmatrix},$$

and $$b_{i,j} = w_{i-1,j} s_{t_i,j}.$$

Each column of $H_{u_1^N}$ represents the contribution from each homopolymeric region to the resultant $x_1, x_2, \ldots, x_N$ versus test number. Explicitly, we can write each column j, $j_{u_1^N,j}$ as a shifted and scaled impulse response in D-transform notation by defining $h_j(D) = \tilde{h}_{u_1^N,j}^T \cdot [\tilde{D}^0 D^1 \ldots D^N]^T$. The impulse response is shifted since the impulse occurs at the time of first incorporation for the corresponding homopolymeric region (i.e., not at time 0), while it is scaled since the length of that homopolymeric region is not necessarily one. In this form, we see that for p<1, each homopolymeric region (or transmitted symbol in the communication analogy) contributes to succeeding output even for very large N, although possibly negligibly.

Figure 11:
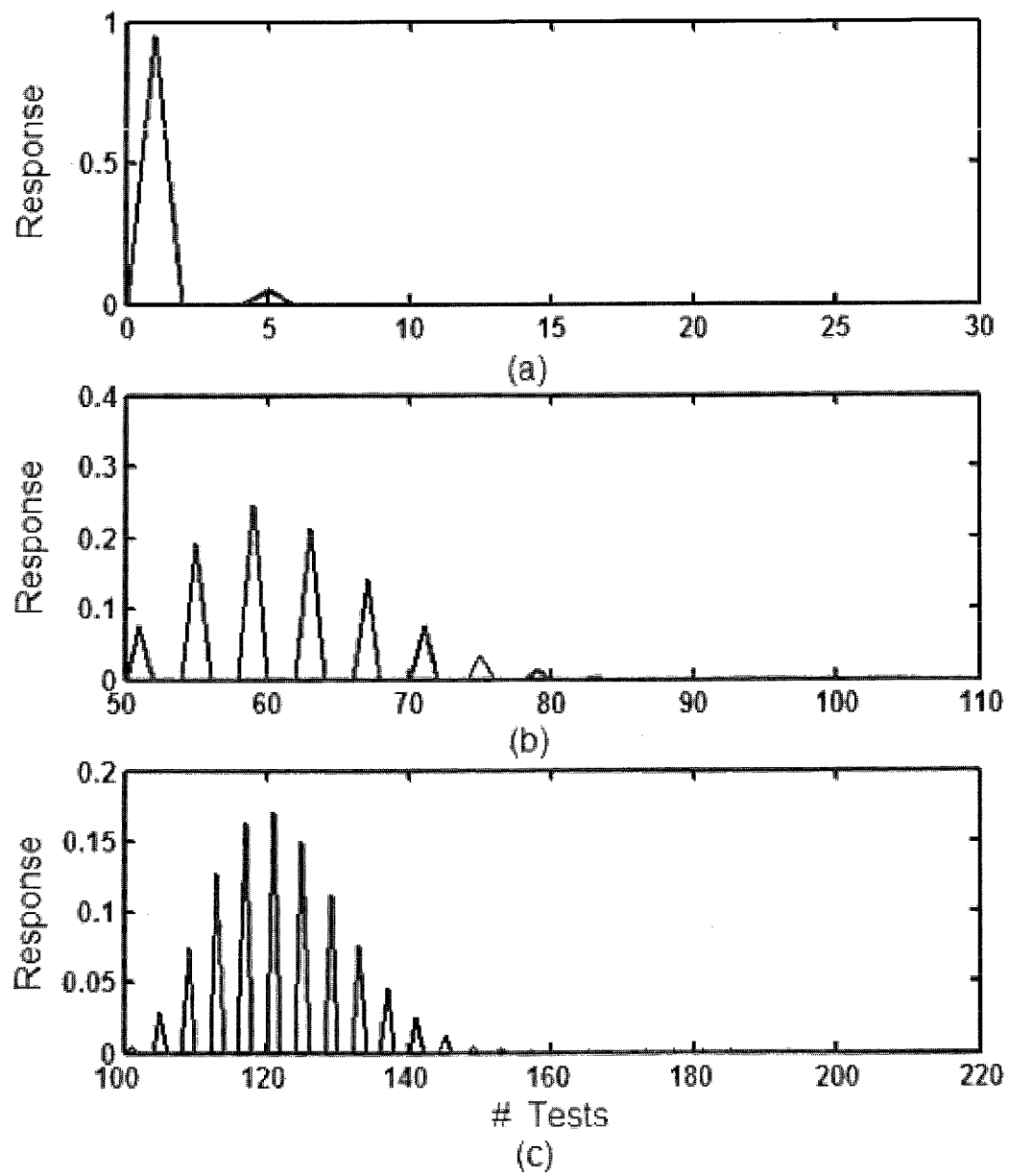
FIG. 11(a) illustrates the evolution of the time-varying impulse response for p=0.95, where ISI is negligible for the first base, consistent with embodiments of the present disclosure.
FIG. 11(b) illustrates the evolution of the time-varying impulse response for p=0.95, where ISI but becomes more severe after 50 tests, consistent with embodiments of the present disclosure.
FIG. 11(c) illustrates the evolution of the time-varying impulse response for p=0.95, where ISI but becomes more severe after 100 tests, consistent with embodiments of the present disclosure.

From FIG. 11, we can visualize this phenomenon by examining the above relation for a specific case. The shifted impulse responses (columns of $H_{u_1^N}$) are plotted for homopolymeric regions 1, 51 and 101, i.e., column 1, 51 and 101 of $H_{u_1^N}$ for that particular sequence. At the beginning of sequencing (see FIG. 11(a)), the channel response is nearly memoryless for p close to one (i.e., approximately a Kronecker delta), while many testing cycles later (see FIGS. 11(b) and (c)), the response is distributed over a wide range of tests. Clearly the overall constraint length of the convolution generated by the channel grows proportionally to read length. Furthermore, it is apparent that even the effective constraint length (non-negligible portion of the impulse response) grows considerably, a daunting characteristic in terms of computation, since MLSD's complexity grows exponentially with constraint length. Looking at computational complexity from the perspective of the incorporation vector, for a moderate constraint length of 20 and K=5, there are nearly $6^{20} \approx 3.6 \times 10^{15}$ possible sequences. In the following section we explore several of the approximate MLSD techniques used in the communication field.

V. Approximate MLSD Algorithm for Base-Calling

Although we cannot perform full-blown MLSD due to computational complexity requirements, we can nevertheless attempt to approximate it, such that we recover some additional information that increases the immunity of the output to noise. The three classes of appropriately modified algorithms we consider are symbol-by-symbol (SBS) detection (following causal equalization), the stack algorithm, and MLSD via the Viterbi algorithm. Before detailing these three algorithms, we first discuss potential computational saving gains through exploitation of the problem model. We then compare the performance of these algorithms in the last part of this section.

A. Exploiting Problem Structure

Figure 12:
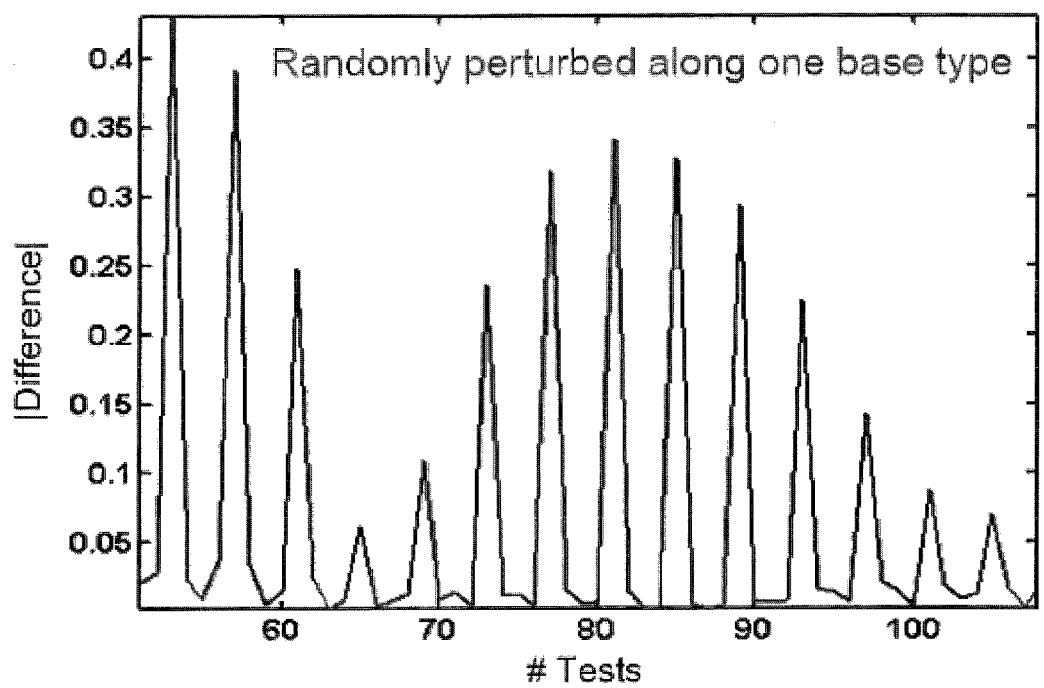
FIG. 12 depicts a plot showing decorrelation between different base types for p=0.99, where a sample sequence is randomly perturbed along only a single base-type and its absolute value of its difference from the original sequence at the output is plotted and where interpeak regions correspond to tests of the 3 other base-types and are only slightly affected by the perturbation, consistent with embodiments of the present disclosure.

In an attempt to lower the complexity of full-blown MLSD, one reasonable question to ask would be, why not process the A, C, G, and T test subsequences independently? In other words, perform whatever decoding/deconvolution technique we would like, but treat the responses from the 4 base-types as completely uncorrelated. This is not feasible in general since given a sequence ACTATA and p=0.8, we would have A signals [0.8 0.5696 0.6218] versus [0.8 0.672, 0.6669] for ATATA. Clearly, the presence of the C base makes a big difference. For p=0.995, on the other hand, the difference between the two, [0.995 0.9851 0.99] versus [0.995 0.99 0.99], is much less significant. FIG. 12 plots the absolute value of the difference between two sequences at the output given one sequence is randomly perturbed along one base-type at the input for p=0.99. The interpeak regions in the plot correspond to the test differences of the 3 other base-types and are only slightly affected by the perturbation. Hence, this plot illustrates how most of the separation distance between output sequences for a given base is aligned along its base-type rather than evenly distributed throughout the sequence for p close to one. As such, under the condition that p is very close to one (which is typically the case in practice) and that we have a reasonable approximation of the intervening sequence, we can separately decode the four different test subsequences. This implies that under these conditions, we can extend our MLSD constraint length, L, by a factor of 4 with only a four times increase in complexity rather than an exponential increase of $(K+1)^{3L}$.

Figure 13:
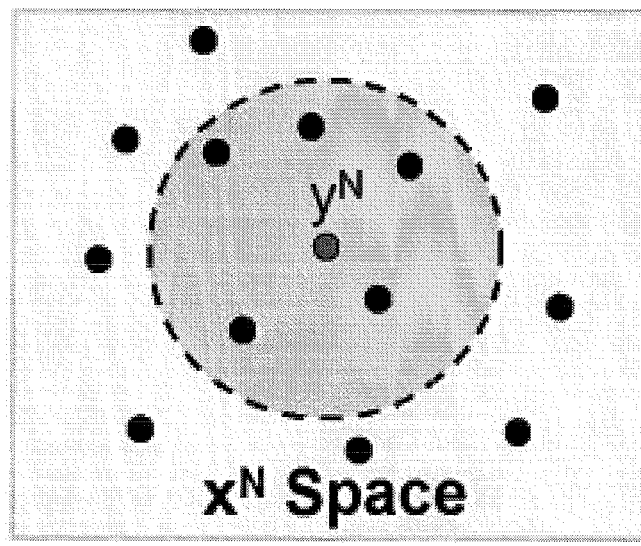
FIG. 13 depicts pruning of search space, i.e., sphere decoding, consistent with embodiments of the present disclosure.

Not only can we exploit the decorrelation between base-types when p is close to one, but we can also exploit the fact that the observed signals, $y_1, y_2, \ldots, y_N$ combined with an estimate of the noise variance $\sigma^2$, reveal information about the input signal power. Indeed, we can prune the input search space drastically since we know that the input signal power, multiplied by the effective impulse response for the stretch of observation variables which we are examining, should give a reasonable estimate of the output signal power. In other words, we can perform sphere decoding or, in this case, Pohst enumeration. Accordingly, given that the point $y=(y_1, y_2, \ldots, y_N)$ lies within a sphere of radius $\kappa$ of $x=(x_1, x_2, \ldots, x_N)$ with probability $1-\epsilon$, when $\kappa > c\sigma$ (c a constant), we can discard all input sequences that correspond to points outside this noise sphere, since they are highly unlikely to be the correct sequence (see FIG. 13). In short, we are searching for the closest lattice point in the skewed output space, $x^N$. Thus, we constrain the search to input sequences, $u_1^N$ that satisfy $$|y-x|^2 \leq \kappa^2, \quad (4)$$

where the relation is constrained to test subsequences of a single base-type.

Computing admissibility of points in the sphere may prove as computationally intensive as simply computing their corresponding metrics in a particular detection algorithm. Thus, we simplify the above expression in two ways: (1) we only consider a portion of the output sequence of length L and (2) we linearize and approximate the channel response around the region of the sequence considered. The latter simplification allows us to fully employ the general Pohst enumeration procedure, whereby the output space is assumed to be a linear transformation of the input space (see the Appendix section for an outline of this procedure). It should be noted however that the savings afforded by sphere decoding in general is proportional to the SNR of the received signal.

B. Approximate MLSD Approaches

We now discuss three approximate ML decoding techniques that we appropriately modify for use with our channel model.

Symbol-by-Symbol Detection:

A zero-order approximation to MLSD is to limit the search set to sequences of length one, or in other words, perform symbol-by-symbol detection (SBSD) following causal equalization. The procedure for SBSD follows the approach for solving for the next transmitted symbol in the absence of noise outlined above, except that the expression is rounded to the nearest integer. Thus, $$u_n = \hat{s}_{t_n, m} = \left\lfloor \frac{x_n - ps'_{t_n} w_{n-1}}{p w_{n-1, m}} \right\rceil,$$

where [•] is the nearest integer function and $m=q(u_1^{n-1}, 0)+1$ as before. This can be thought of as causal zero-forcing equalization (ZFE). The main advantage of this approach is its simplicity, since only one expression must be calculated per test for base-calling. Furthermore, SBSD can be implemented online without delay and thus can be used to generate immediate estimates of the underlying sequence. Of course, as with ZFE in practice, unreliable estimates can result when SNR is especially low largely due to the high susceptibility to error propagation in this regime.

MLSD via Greedy Algorithms:

There are a number of greedy algorithms which can be used to approximate MLSD and that are often employed in the communication field for channels with long time dispersions. A representative example is the stack algorithm. In this algorithm, a finite number of minimum distance paths along with their respective metrics are stored in a stack from best to worst, where each path in this case consists of the respective values of $u_n$ chosen in response to each test. The path with minimum path metric (at the top of the stack) is deleted and extended at each iteration (with K+1 possibilities). These K+1 paths and their associated metrics are then added to the stack. In this way, the stack is continually ordered from least cost to highest, and the path at the top is extended at each iteration. Since only a finite number of paths are kept, higher cost paths are discarded. The number of paths stored can be increased to indirectly extend the effective sequence length that the algorithm considers. However, the storage requirements roughly grow exponentially with the stack algorithm's effective sequence length of consideration, although at a smaller rate than with optimal MLSD. Additionally, the stack algorithm can be used quite effectively with Pohst enumeration as outlined in.

Iterative Partial-MLSD:

Finally, we consider the soft-input Viterbi algorithm (VA) appropriately modified to exploit the problem structure. We choose a symbol length 4L, which is long enough to capture most of the time dispersion in the channel and short enough to meet complexity constraints. We then modify the general VA by using 4 trellises each with symbol length L, thus each having $(K+1)^L$ possible states. We first perform SBSD as outlined above to obtain a rough estimate of the sequence. We then proceed to perform the standard VA on each of the four trellises, with the best surviving paths from the other three trellises (or the rough estimate as available) filling in the gaps. We extend the paths one path length at a time and iterate through the trellises based on the order specified by the test vector, t. Trellis states (of length L) corresponding to 4L length sequences are pruned appropriately (in accordance with our noise sphere) so that highly improbable states are not traversed saving computation time. In this manner, we approximate MLSD using an iterative, partial-MLSD approach.

In many cases, the marginal distribution (or an approximation thereof) for each symbol (i.e, each base) would be of benefit, especially for later DNA assembly algorithms that use consensus estimates obtained from multiple overlapping reads. For instance, this is performed for Sanger sequencing, whereby a confidence score for each base is output. Accordingly, a soft-input soft-output (SISO) variant of the above approach can be used, such as soft-output VA (SOVA) or List VA (LVA), if such confidence measures are so desired. Furthermore, such soft-output can be used to further refine the estimated sequence, if additional a priori information about the underlying sequence is known, such as invalid codewords, in an iterative approach akin to iterative Viterbi for the decoding of concatenated codes.

C. Performance Comparison

Figure 14:
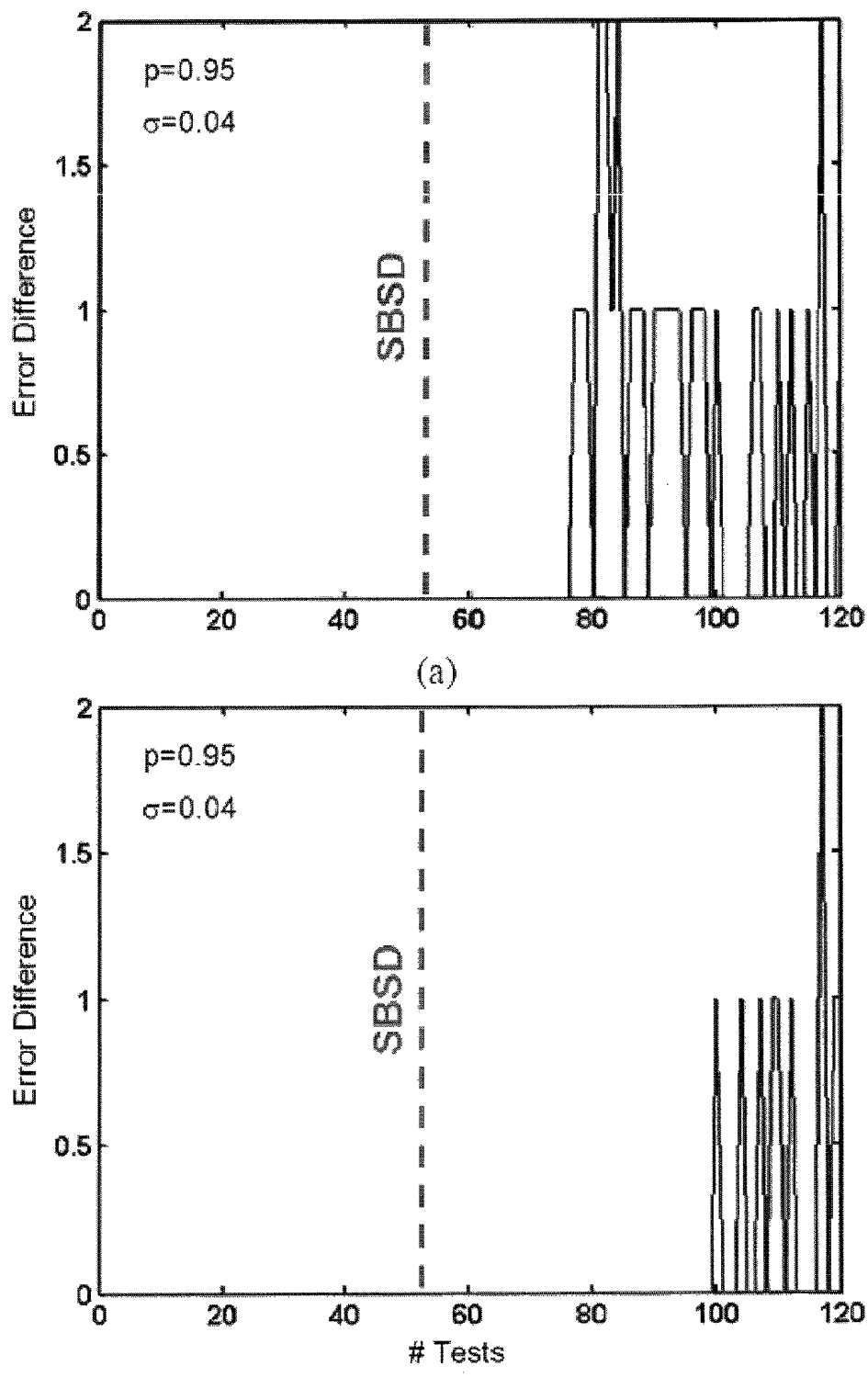
FIG. 14(a) illustrates a performance comparison between SBSD and the Stack algorithm, where the dashed line represents the end of the error-free region for SBSD, consistent with embodiments of the present disclosure.
FIG. 14(b) illustrates a performance comparison between SBSD and partial-MLSD, where the dashed line represents the end of the error-free region for SBSD, consistent with embodiments of the present disclosure.
Figure 15:
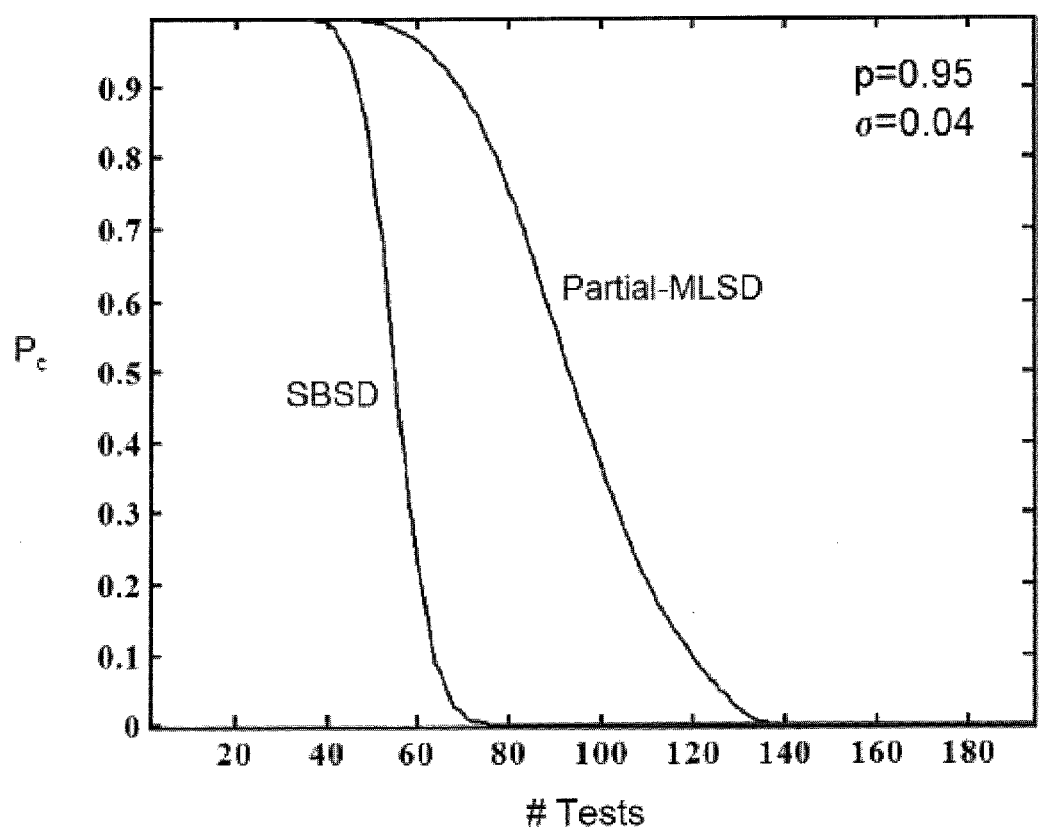
FIG. 15 depicts a Monte-Carlo simulation showing $P_c$ performance for SBSD and partial-MLSD, consistent with embodiments of the present disclosure.
Figure 16:
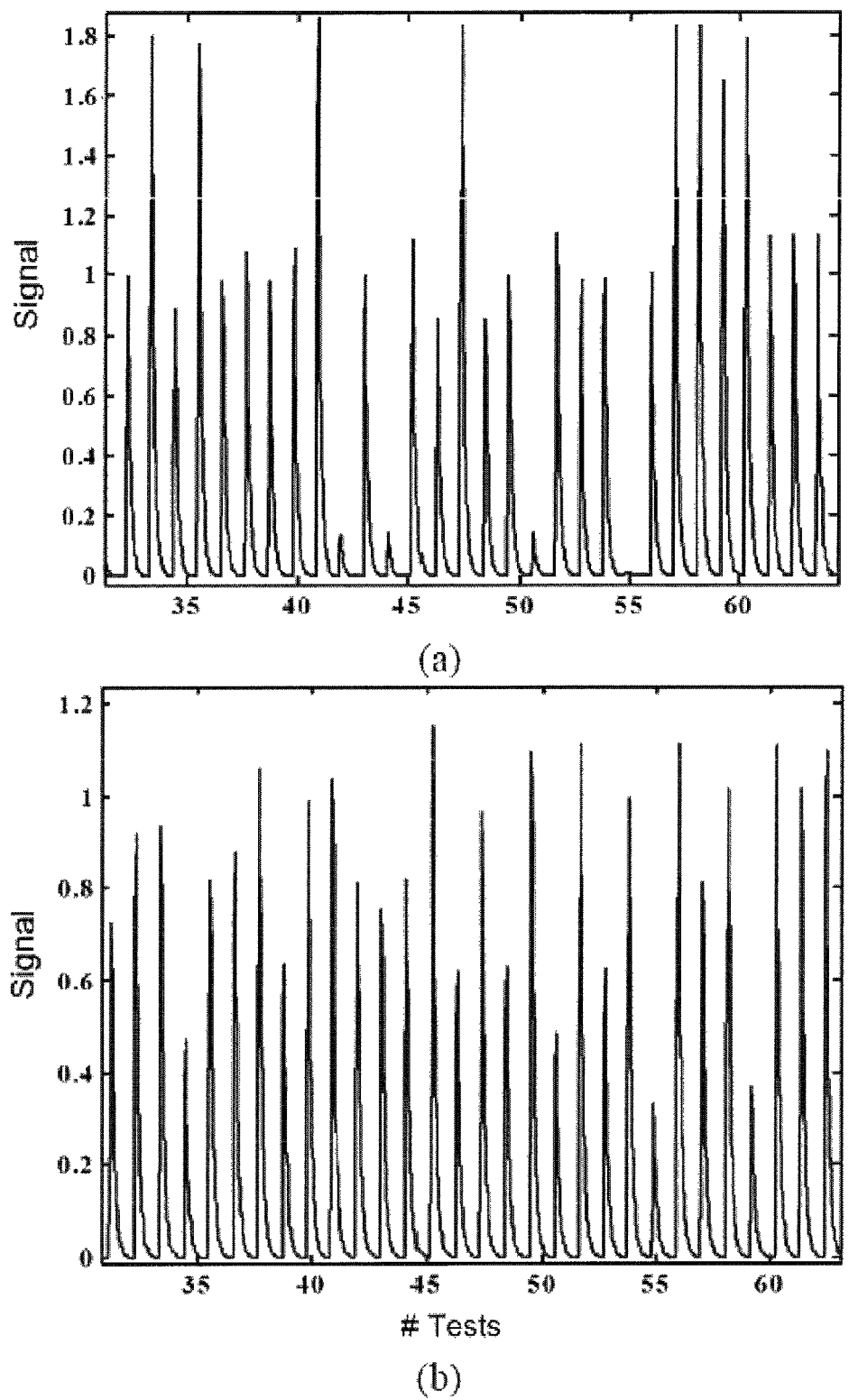
FIG. 16(a) depicts a simulated Pyrosequencing output with $\sigma=0.04$ for p=0.995, consistent with embodiments of the present disclosure.
FIG. 16(b) depicts a simulated Pyrosequencing output with $\sigma=0.04$ for p=0.95, consistent with embodiments of the present disclosure.

FIG. 12 shows a comparison of the SBSD approach versus the stack algorithm and iterative partial-MLSD. These plots show typical results for a particular simulated sequence with p=0.95 and σ=0.04. Clearly, both approximate MLSD algorithms outperform SBSD quite a bit with the iterative partial-MLSD technique performing best. Although p is much closer to one in practice, a smaller p was chosen for illustrative convenience, since signal degradation occurs much more quickly. FIG. 15 shows the results of a 10,000 test input vector Monte Carlo simulation comparing SBSD to MLSD performance in terms of the probability of correct decoding ($P_c$) versus the number of tests (a rough measure of read length). To illustrate the efficacy of all of these algorithms, FIG. 16 shows the output around test 50 for the sample sequence of FIG. 14. Clearly, the existing adaptive bandpass filtering or manual base-calling techniques would be futile in this highly distorted signal regime. Unfortunately, the computational complexity of full MLSD is just too prohibitive even for a comparative study under this simulated setting. In the next section, we bound the probability of correct decoding for SBSD and MLSD.

VI. Bounds on the Probability of Correct Decoding

The obvious question to ask at this point is, how many bases can we reliably call? We can answer this question by further exploiting the communication-theoretic framework with which we have couched the entire sequencing-by-synthesis model. It was mentioned that we can think of the channel input as an uncoded M-PAM constellation with the channel itself introducing severe ISI due to the incomplete incorporation phenomenon. With this idea in mind, we can derive relations for the probability of a single symbol error and then use that result to derive bounds on the probability of correct decoding, $P_c$, for SBSD and MLSD.

First we calculate the probability of error for one symbol given the rest of the sequence is correct. Mathematically, we express this as $$P(\hat{u}_n \neq u^*_n | \hat{u}_1^{n-1} = u^{*n-1}_1, \hat{u}_{n+1}^N = u^{*N}_{n+1}, y_1^N),$$

where we write the decoded symbols as $\hat{u}_n$ and the correct transmitted symbol as $u^*_n$. Thinking about what this means further, given we are certain about all but one homopolymeric region in the entire sequence, the difference between symbol $u_n$, being equal to a 0, 1, . . . , or K, is essentially a difference represented by a multiple of only its impulse response. Thus, at the channel output in the $x^N$ space, we still have an M-PAM constellation with minimum distance captured by the impulse response of the symbol in question. As such, we can directly use the probability of error result for M-PAM channels to ascertain that $$P(\hat{u}_n \neq u^*_n | \hat{u}_1^{n-1} = u^{*n-1}_1, \hat{u}_{n+1}^N = u^{*N}_{n+1}, y_1^N) \approx \frac{2(M-1)}{M} Q\left(\frac{d_{min}(n)}{2\sigma}\right),$$

where $d_{min}(n)$ is the distance to the closest sequence with respect to the nth symbol and is a function of its impulse response, σ is the noise level, N is the total length of the observed output sequence, and M=K+1 is the number of symbols. The approximation results from the non-linearity of an incorporation event in the model, that is, the minimum distance between $u_n=0$ and $u_n=1$ is slightly different (larger) than that of the other symbol separation lengths. The shorter distance can be used to produce a conservative estimate of the probability of error.

A. Lower Bound on $P_c$ for SBSD In order to ascertain the efficacy of SBSD in terms of some measure of the attainable read-length, we must first calculate the probability of symbol error. Given the past sequence is correct and that our model is accurate, the remaining uncertainty lies only in the determination of the current symbol. That is, was it 0, 1, . . . , or K? We can write this probability as $P(\hat{u}_n \neq u^*_n | \hat{u}_1^{n-1} = u^{*n-1}_1, y_1^N)$. This boils down to M-PAM with minimum distance between received symbols in this case given by p times the weight of the leading group, $w_{n-1,m}$, where $m=q(u_n^{n-1},0)+1$ is again the position of the ideal subgroup in $w_n-1$. Accordingly, we can derive a lower bound on the probability of correct decoding (i.e., the probability we have not made a single error) versus the number of tests since $$P(\hat{u}_1^n = u_1^{*n} | y_1^N) = \prod_{i=1}^n P(\hat{u}_i = u^*_i | \hat{u}_1^{i-1} = u_1^{*i-1}, y_1^N)$$

$$\geq \prod_{i=1}^n P(\hat{u}_i = u^*_i | \hat{u}_1^{i-1} = u_1^{*i-1}, y_1^i)$$

-continued $$= \prod_{i=1}^{n} \left(1 - \frac{2(M-1)}{M} Q\left(\frac{pw_{i-1,m}}{2\sigma}\right)\right)$$

$$\geq \prod_{i=1}^{n} \left(1 - \frac{2(M-1)}{M} Q\left(\frac{p^i}{2\sigma}\right)\right).$$

Figure 17:
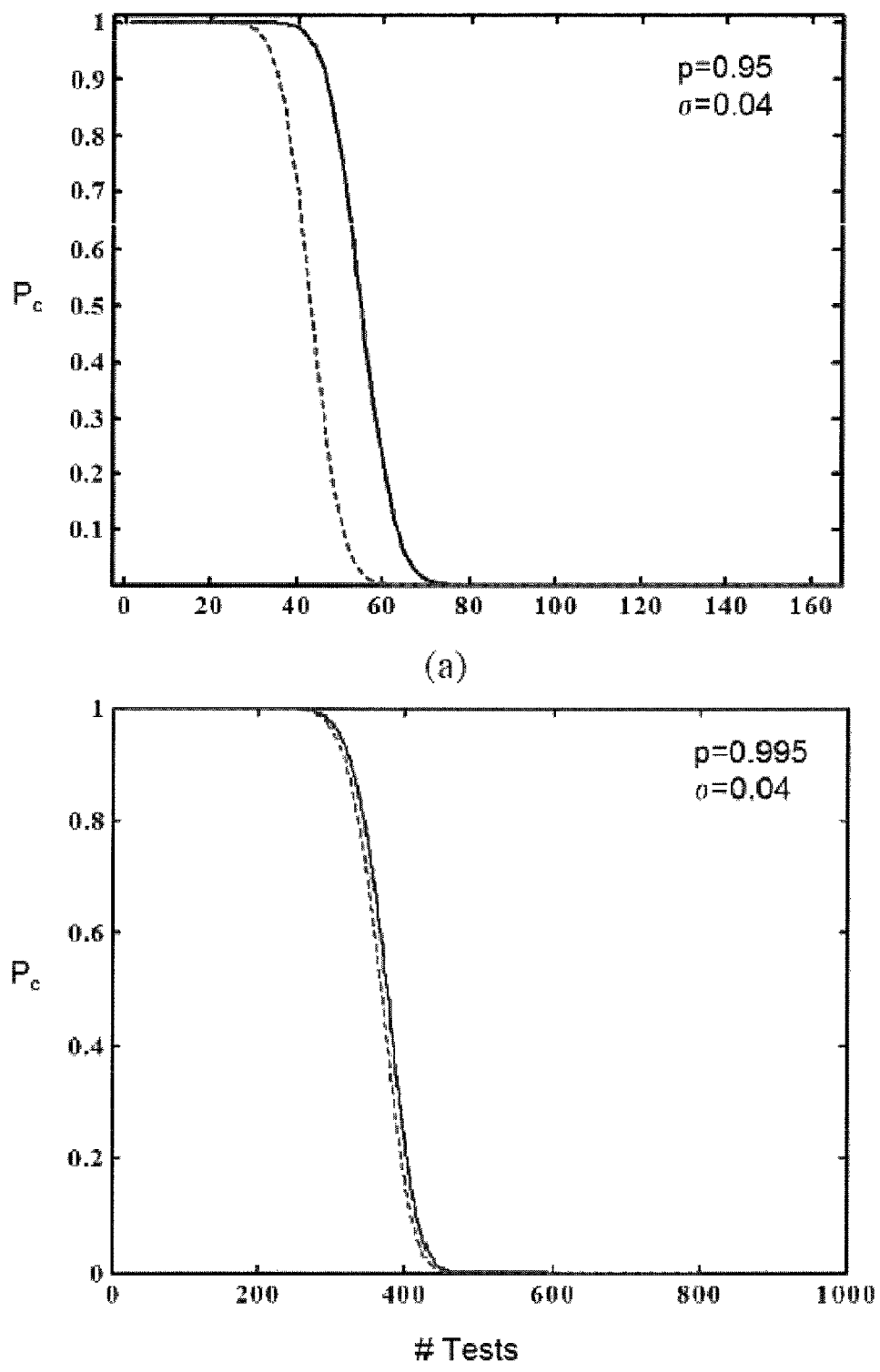
FIG. 17(a) illustrates the probability of correct decoding for SBSD versus the number of tests for p=0.95, where the dotted line shows the lower bound approximation, consistent with embodiments of the present disclosure.
FIG. 17(b) illustrates the probability of correct decoding for SBSD versus the number of tests for p=0.995, where the dotted line shows the lower bound approximation, consistent with embodiments of the present disclosure.

The last inequality follows since we can lower bound the minimum distance for SBS, $pw_{n,m}$, by $p^n$. FIG. 17 plots $P_c$ versus the number of tests for two cases, p=0.95 and p=0.995. The dotted curve represents the $d_{min}$ approximation and is a good fit for p close to one. Notice the effect p has on the accuracy of base-calling: a change of p from 0.95 to 0.995 represents a seven-fold improvement in the length of high-accuracy decoding.

B. Bounds on Pc for MLSD

Figure 18:
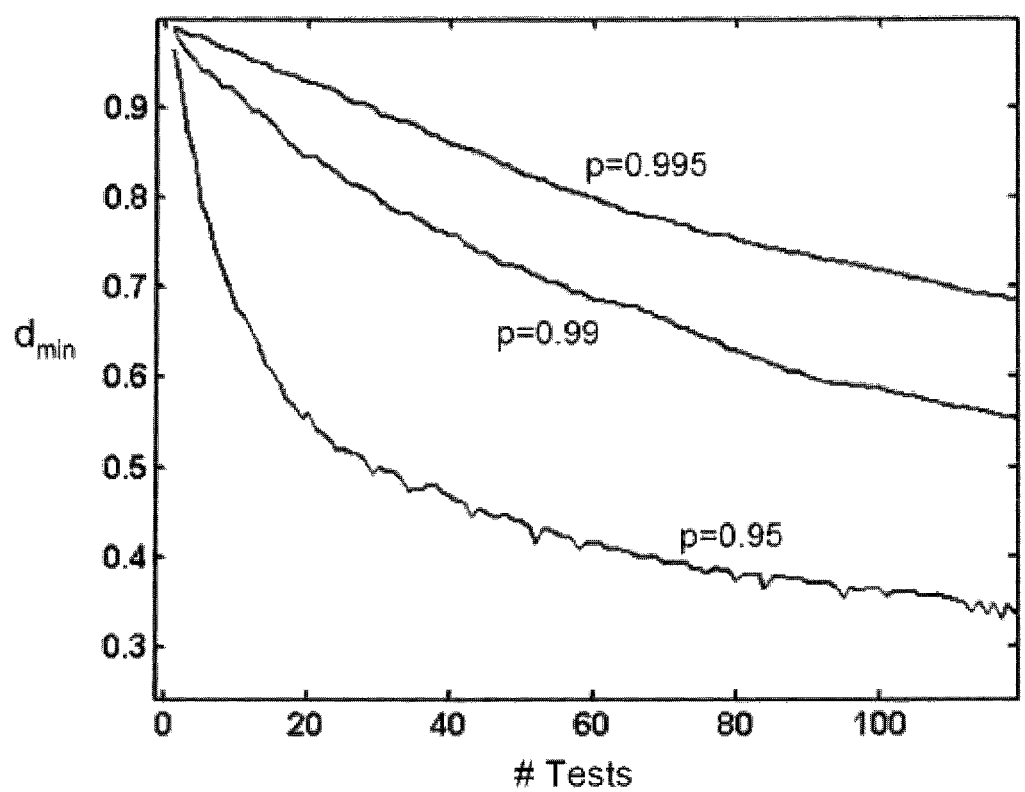
FIG. 18 contains a plot showing $d_{min}$ as a function of the number of tests for various values of p, consistent with embodiments of the present disclosure.

We can further this analysis to derive probability of correct decoding bounds for MLSD. We know from equation (5) that the probability of error is dependent on $d_{min}$. As alluded to above, calculating $d_{min}$ for MLSD involves finding the impulse response for a given symbol, since that characterizes the $l_2$ distance between two output sequences. Alternatively $d_{min}$ can be thought of as the $l_2$ distance between respective x's, when input symbol $u_n$ is perturbed by one unit. FIG. 18 plots $d_{min}$ as a function of the number of tests for various values of p. We can now derive an upper-bound on the probability of correct decoding for MLSD. This bound is optimistic as it uses the "one-shot" probability of error in its derivation, which essentially ignores the reduction in $d_{min}$ due to ISI. Accordingly, $$P(\hat{u}_1^n = u_1^{*n} | y_1^N) \leq P(\hat{u}_i^n = u_i^{*n} | \hat{u}_{n+1}^N = u_{n+1}^{*N}, y_1^N)$$

$$= \prod_{i=1}^{n} P(\hat{u}_i = u_i^* | \hat{u}_{i+1}^N = u_{i+1}^{*N}, y_1^N)$$

$$\leq \prod_{i=1}^{n} P(\hat{u}_i = u_i^* | \hat{u}_1^{i-1} = u_1^{*i-1}, \hat{u}_{i+1}^N = u_{i+1}^{*N}, y_1^N)$$

$$= \prod_{i=1}^{n} \left(1 - P(\hat{u}_i \neq u_i^* | \hat{u}_1^{i-1} = u_1^{*i-1}, \hat{u}_{i+1}^N = u_{i+1}^{*N}, y_1^N)\right)$$

$$\approx \prod_{i=1}^{n} \left(1 - \frac{2(M-1)}{M} Q\left(\frac{d_{min}(i)}{2\sigma}\right)\right).$$

Figure 19:
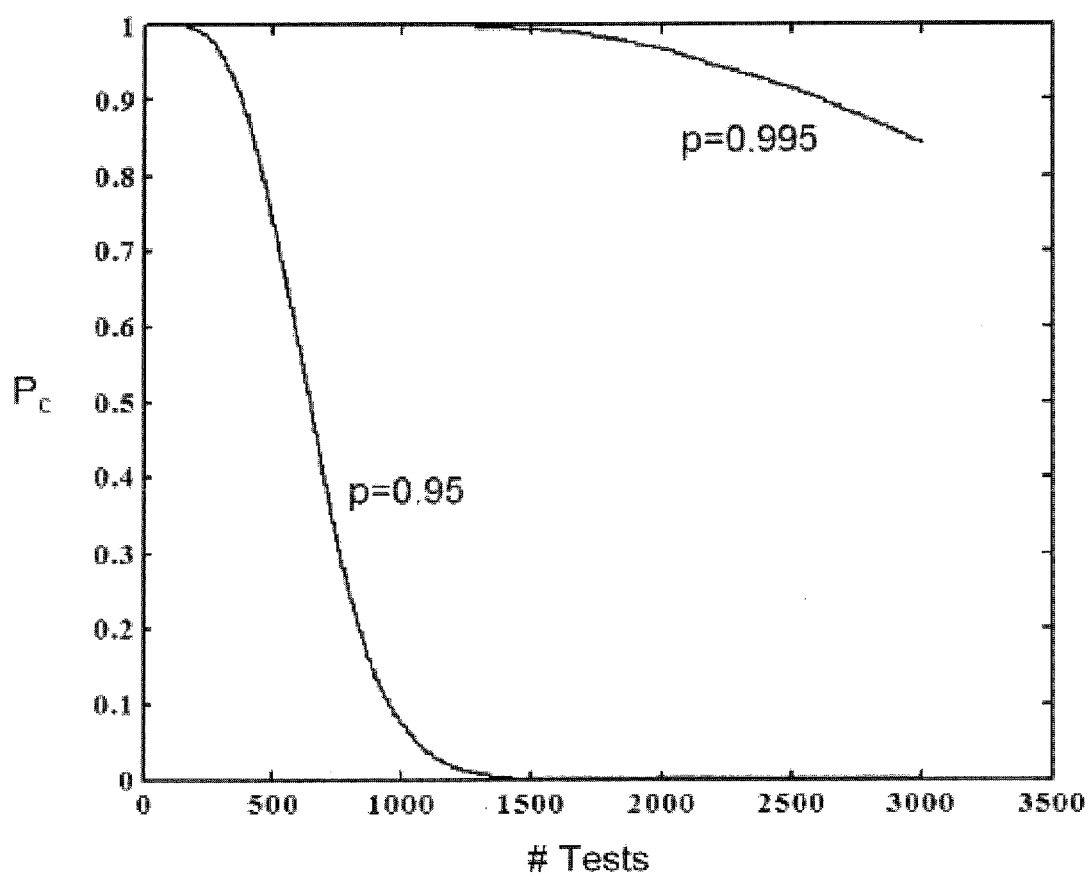
FIG. 19 shows a loose upper bound on $P_c$ for MLSD decoding for p=0.95 and p=0.995, consistent with embodiments of the present disclosure.

FIG. 19 plots the above upper bound for two different incorporation rates and $\sigma$=0.04.

Figure 20:
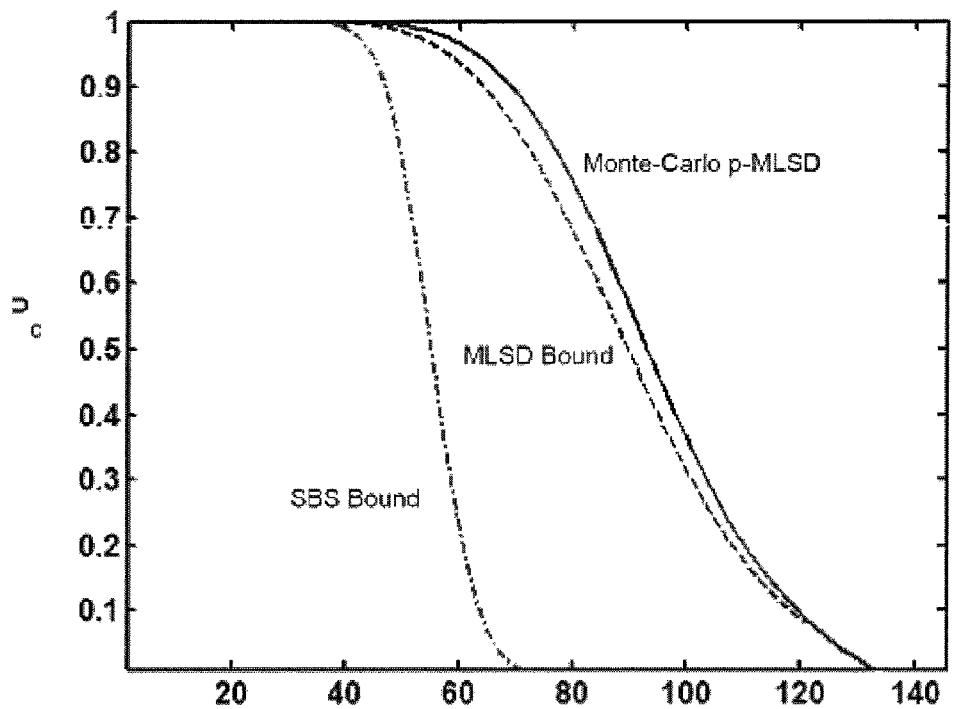
FIG. 20(a) contains a plot showing MLSD $P_c$ approximation versus partial-MLSD Monte Carlo simulation and lower bound for SBSD for p=0.95, consistent with embodiments of the present disclosure.
FIG. 20(b) contains a plot showing MLSD $P_c$ approximation versus partial-MLSD Monte Carlo simulation and lower bound for SBSD for p=0.995, consistent with embodiments of the present disclosure.
Figure 20:
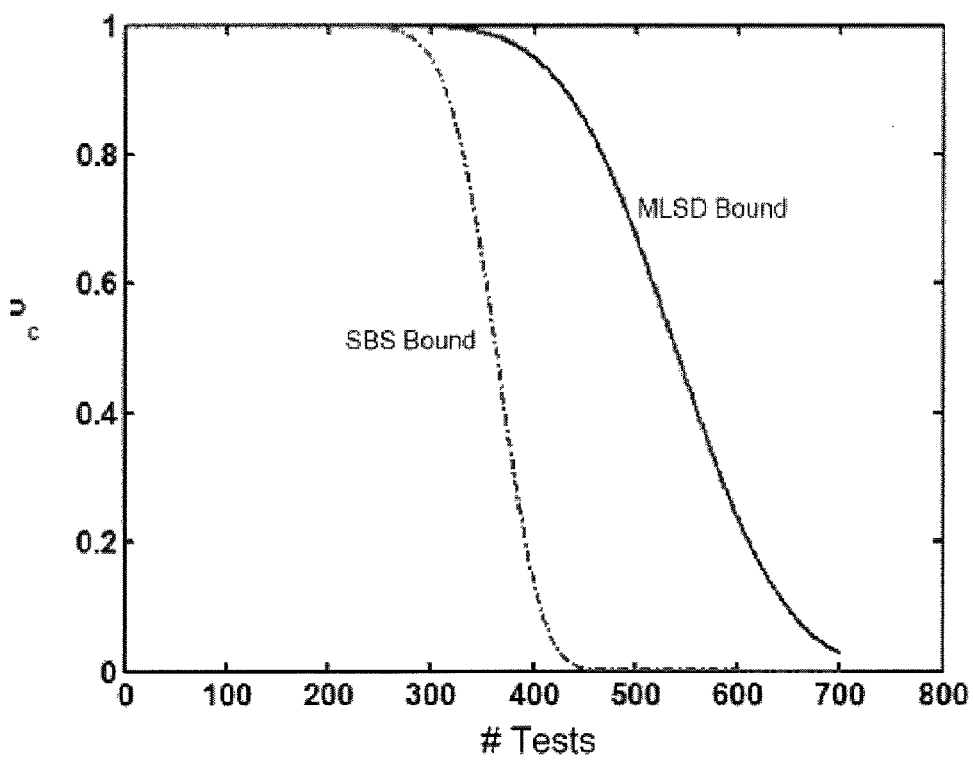

The bound presented above is quite optimistic and it is clear from the Monte-Carlo simulation presented in FIG. 15 that the iterative partial-MLSD method, although outperforming SBSD, falls quite short from it. One of two conclusions can be drawn: either the algorithm itself can be improved dramatically or the adverse effects of ISI are too severe to combat. To investigate this more closely, we must analyze the effect of ISI on $d_{min}$. To do this, we need to find the time-varying channel impulse response, $h_m(D)$, for a specific sequence and testing order. We choose the worst-case sequence and testing order, that is, the example case of equation (3) with incorporation occurring at each test, since this produces the widest dispersion for a given number of tests. We then calculate the worst-case ISI on this channel by performing an exhaustive search through all error sequences of length l, ($\epsilon_0, \epsilon_1, \ldots, \epsilon_{l-1}$). The worst-case ISI is the error sequence with the minimum metric. This metric represents the minimum distance between the true sequence and the next closest sequence (with errors in only the last l symbols). Explicitly, $$d_{min-ISI}(n) \approx \operatorname*{argmin}_{\varepsilon} \left\| \sum_{i=n}^{n+l-1} h_{m(i)}(D)\varepsilon_{i-n} D^{i-n} \right\|,$$

where $m(i)=q(u_1^{i-1},0)+1$. Now $d_{min-ISI}(n)$ can be used to provide a better approximation of MLSD performance with the adversities of ISI considered. FIG. 20(a) plots this approximation as well as the lower bound for SBSD against the Monte-Carlo performance of the partial-MLSD algorithm for p=0.95. As can be seen, the MLSD error approximation is quite close to the empirical performance of the partial-MLSD algorithm. FIG. 20(b) compares MLSD to SBSD for p=0.995. These plots also suggest that a significant portion of the channel's ISI cannot be combated.

VII. Experimental Results

Figure 21:
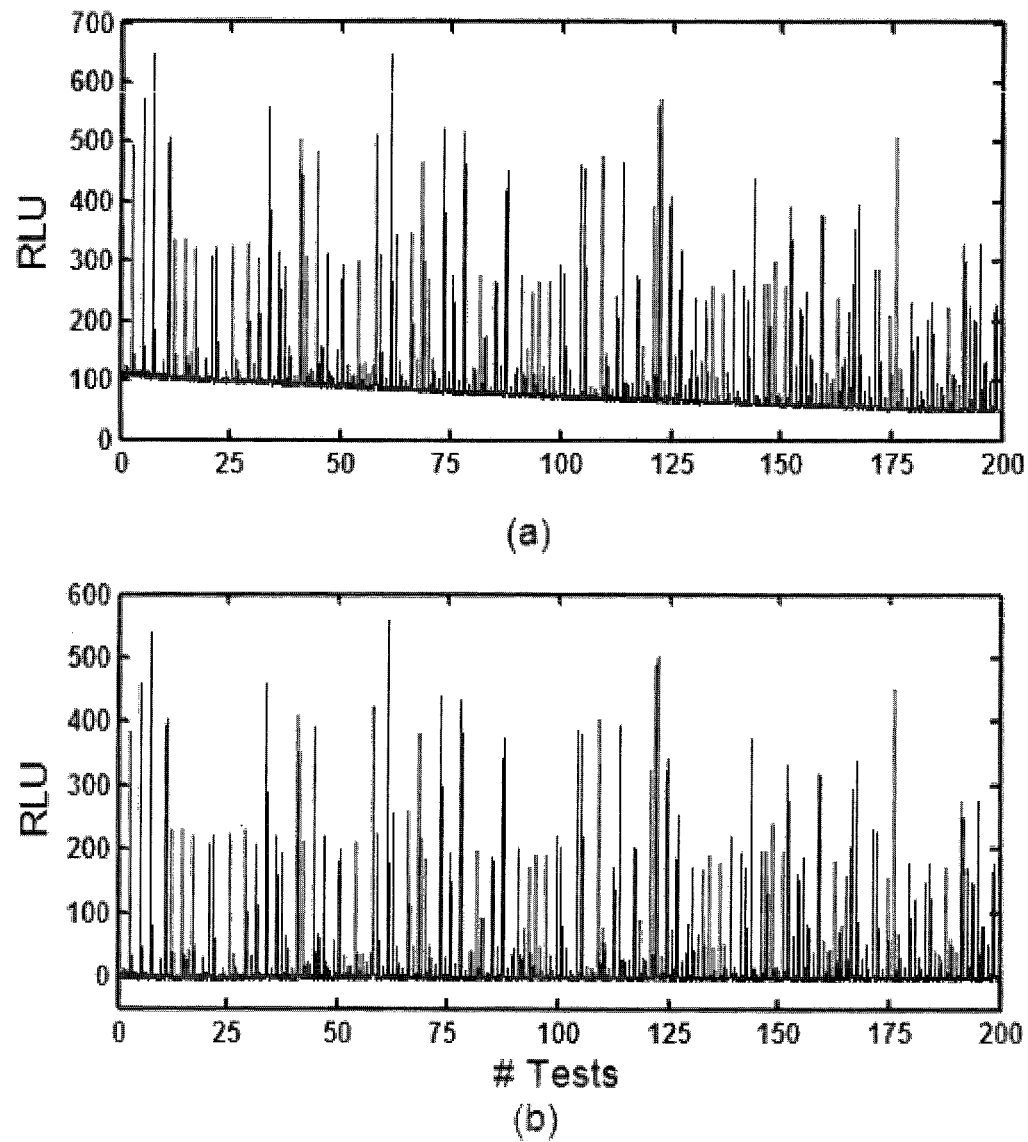
FIG. 21(a) shows experimental Pyrosequencing data in relative units (RLU) before correction, consistent with embodiments of the present disclosure.
FIG. 21(b) shows experimental Pyrosequencing data in relative units (RLU) after correction, consistent with embodiments of the present disclosure.

In order to perform the iterative partial-MLSD algorithm on real biological Pyrosequencing data, there are a few practical issues which must be considered. First of all, a baseline correction must be performed due to the changing chemical background signal present. This causes a slow exponential decay versus time of the baseline. The correction is performed by subtraction of the approximate baseline obtained via interpolation of the smoothed interpeak segments. Next, integration of the entire signal is required since the peak values are in general not directly proportional to the total area under the curve, i.e., the total photoemission for that incorporation. Finally, we must complete our model with the necessary experimental parameters, e.g., p, nucleotide specific gains, etc., fitted from empirical training data with known underlying sequences. FIG. 21 shows experimental sequencing data before and after baseline correction.

Figure 22:
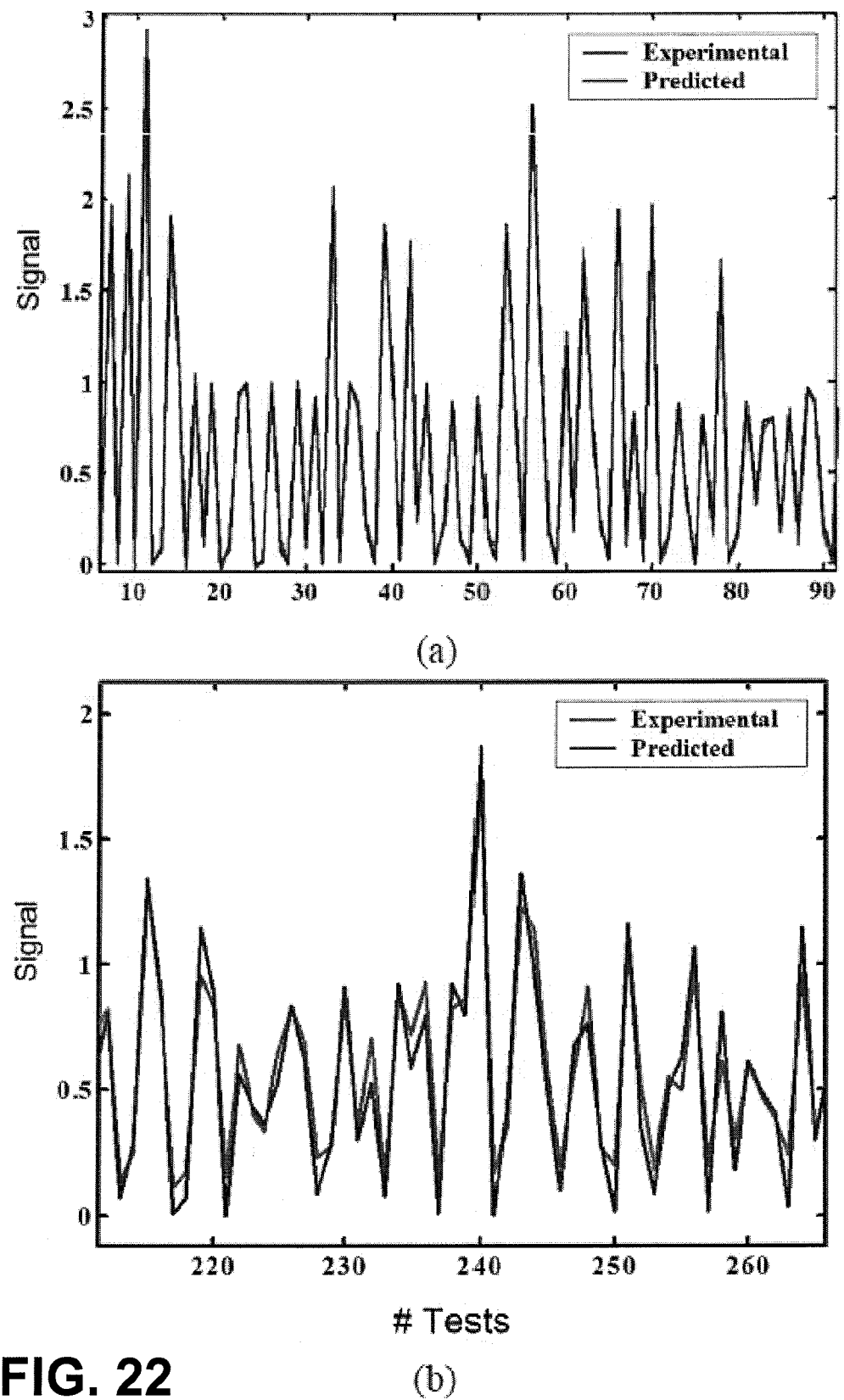
FIG. 22 contains plots showing accuracy of predicted output versus experimental data in two different regions of the DNA sequence, consistent with embodiments of the present disclosure.
Figure 23:
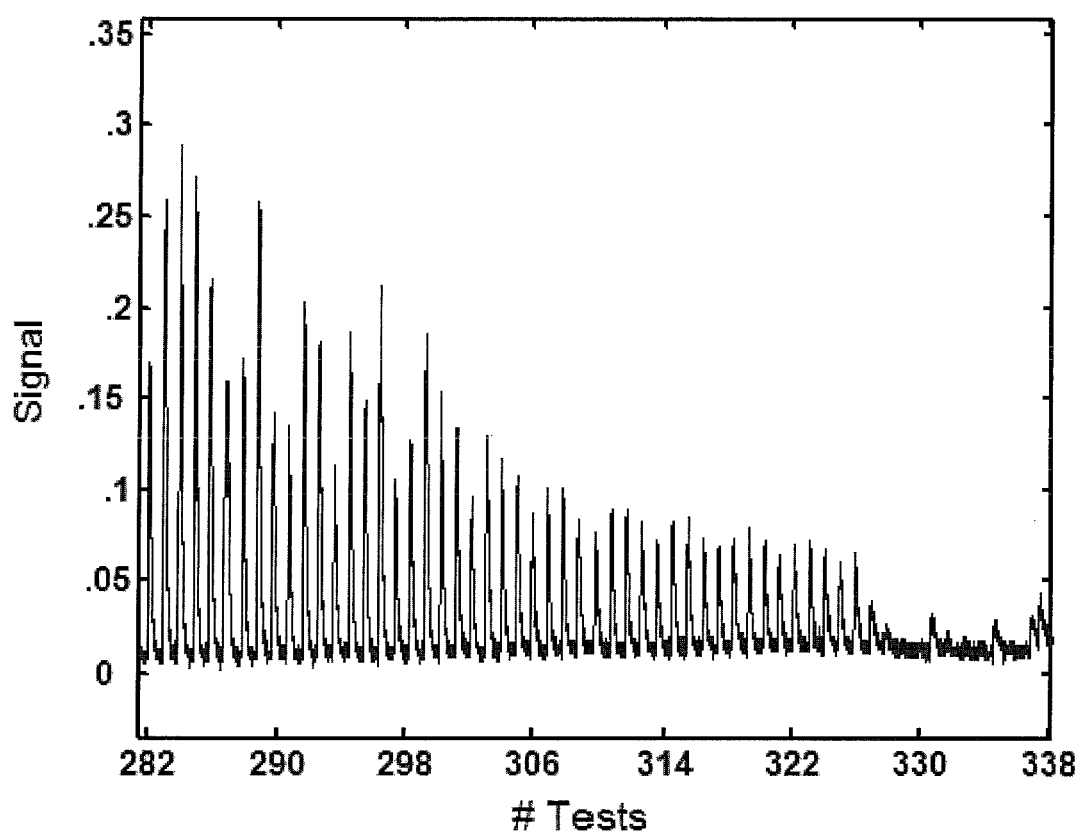
FIG. 23 shows experimental Pyrosequencing output showing breakdown in chemistry due to the adversities of product inhibition and accumulation, consistent with embodiments of the present disclosure.

We applied the iterative partial-MLSD approach to the experimental Pyrosequencing data shown in FIG. 21(b). The sequenced template consisted of a 208 base length polymerase-chain reaction (PCR) product. The incorporation rate was determined to be close to 0.995 for this particular system setup and $\sigma \approx 0.05$. The algorithm correctly decoded the first 280 tests without error (see FIG. 22). This corresponds to error-free sequencing of the first 170 bases. This is quite an improvement over the 30-40 bases that are typically reliably sequenced with commercial Pyrosequencing machines. Unfortunately, due to the prototype system's limitations, product inhibition rather than incomplete incorporation prevented any longer reads, as the signal quality degrades quickly in that regime (see FIG. 22). This can be solved though using systems which implement slightly better reagent handling techniques. With such a system in conjunction with improved base-calling algorithms such as detailed herein, read lengths well over 200-300 bases should be attainable with Pyrosequencing. Such read lengths would make DNA sequencing-by-synthesis methods a potentially much higher throughput and much more cost effective alternative to the existing techniques.

APPENDIX SECTION

Sphere Decoding Approximation

To perform Pohst Enumeration, we can approximate the inequity (4) by $$|y' - Bu_{N-L+1}^N|^2 \leq \kappa'^2,$$

Where B=Toeplitz($h_{u_{N-L+1},m^N}$)D, m=q($u_1^{N-L}$,0)+1 is the position of the ideal subgroup in $W_{N-L}$ after N-L tests, D=diag(p, $p^3$, $p^5$, $p^7$, ... ), $$Toeplitz([a_1, a_2, \ldots, a_n]) = \begin{bmatrix} a_1 & 0 & \ldots & 0 \\ a_2 & a_1 & \ldots & 0 \\ \vdots & \vdots & \ddots & \vdots \\ a_n & a_{n-1} & \ldots & a_1 \end{bmatrix},$$

L is the considered constraint length and the impulse response vector $h_{u_{N-L+1},m^N}$ is obtained from a first-pass symbol-by-symbol (SBS) estimate. A more refined estimate can be obtained by setting B to the appropriate subset of matrix $H_{u_1^N}$ (also derived from the SBS estimate). The primes on $Y^1$ and $K^1$ result from subtracting off the contributions of the first m−1 subgroups, that is, subtracting from y the row-wise sum of the first m−1 columns of $H_{u_1^N}$ and then taking the inner product of that sum and subtracting that from $k^2$. This gives us a triangular system of linear inequalities which can be back-substituted to solve for the admissible value of $u_{N-L+1}^N$.

In various embodiments, underlying DNA sequences are characterized using an approach as follows to model the detection of pyrophosphate and corresponding non-idealities.

Sequencing Base-Calling Problem:

Given: $Y_1, \ldots, Y_N$, where $Y_i = X_i + N_i$, where the $X_i$ are the sum of all PPi released at a given nucleotide addition i corresponding to base B(i mod 4), $N_i$ is iid Gaussian distributed noise ($\mathcal{N}(0, \sigma_n^2)$) and B(1)='A', B(2)='C', B(3)='G', B(4)='T'.

Given: Process modeled by incomplete incorporation phenomenon with known rate p, where 0<p<=1.

Estimate: $S_N$, the sequence vector corresponding to the maximum a posteriori DNA sequence given $Y_1, \ldots, Y_N$, where $S_i = 0, \ldots, K$, where K is the maximum multiplicity of bases incorporated in a single addition.

Approach: In order to better model the situation, a weight vector, $W_N$, is designated, whose components $w_N(i)$ correspond to the fraction of starting DNA present at time N with characteristic lag m−i. For instance, the table in Example 2, lists the corresponding state vector for a specific DNA sequence versus time (nucleotide additions). Thus, $W_N$ corresponds to the hidden state of the system at time N.

Let us first define the matrix $T_N$, which is a one-to-one transformation of the sequence vector, $S_N$:

$$T_N(i, j) = \begin{cases} S_N(j) & \text{if } i = i \bmod 4 \\ 0 & \text{otherwise} \end{cases}$$

We then crop all zero columns from $T_N$, producing $U_N$ with m<=N columns.

Furthermore, since $X_N$ is the sum of all pyrophosphate molecules released in a single addition, we can relate X to w as follows:

$$X_N = p U_N (N \bmod 4)^T w_{N-1}.$$

We now must relate the current state to previous states in order to iteratively propagate the model. The hidden states, $W_i$ at time i, are a function of $W_{i-1}$ in that there are only two possibilities: either each component (DNA group with a particular lag) of $W_{i-1}$ incorporates the added nucleotide B(i mod 4) with rate p or it is unaffected by the addition. More precisely, $w_N = [w_N(1) \ldots w_N(i) \ldots w_N(m)]^T$, where $w_N(i) = pI(U_N(i-1,N \bmod 4)) \cdot w_{N-1}(i-1) + (1-pI(U_N(i,N \bmod 4)) \cdot w_{N-1}(i)$.

It is possible to derive a non-recursive relation between $X_N$ and the input sequence:

$$X_N = \sum_{i=0}^{N(S_N, N\bmod 4)} \left[ \binom{m - q(S_N, i) + i - 1}{i} p^{m-q(S_N,i)} (1-p)^i \cdot U_N(m - q(S_N, i), N\bmod 4) \right].$$

N(a,b) is a function which returns the number of non-zero incorporations in the sequence vector, a, equivalent to base B(b), q($S_N$, i) returns the number of non-zero entries in SN from component N up to N−4i, and m is the total number of columns in UN.

Armed with the above model, we can now attempt to find the sequence vector, $S_N^*$ which maximizes the a posteriori probability, $$P(U_N | Y, \ldots, Y_N).$$

$$\begin{aligned} S_N^* &= \underset{S_N}{\operatorname{argmax}} P(S_N | Y_1, \ldots, Y_N) \\ &= \underset{S_N}{\operatorname{argmax}} P(Y_1, \ldots, Y_N | S_N) P(S_N) \\ &= \underset{S_N}{\operatorname{argmax}} P(X_1 + N_1, \ldots, X_N + N_N | S_N) P(S_N) \\ &= \underset{S_N}{\operatorname{argmax}} \prod_{i=1}^{N} P(X_i + N_i | S_i) P(S_N(i)) \\ &= \underset{S_N}{\operatorname{argmax}} \sum_{i=1}^{N} \ln P(S_N(i)) + \ln P(X_i + N_i | S_i) \\ &= \underset{S_N}{\operatorname{argmax}} \sum_{i=1}^{N} \ln P(S_N(i)) + \ln \frac{1}{\sqrt{2\pi} \sigma_n} e^{-\frac{(Y_i - pU_N(i\bmod 4)^T w_{i-1})^2}{2\sigma_n^2}} \\ &= \underset{S_N}{\operatorname{argmax}} \sum_{i=1}^{N} 2\sigma_n^2 \ln P(S_N(i)) - (Y_i - pU_N(i\bmod 4)^T w_{i-1})^2 \\ &= \underset{S_N}{\operatorname{argmax}} \sum_{i=1}^{N} (Y_i - pU_N(i\bmod 4)^T w_{i-1})^2, \end{aligned}$$

when $P(S_N(i)) = P(S_N(j))$ for $i \neq j$.

Note that $U_N$ is an implicit function of $S_N$. In the last line above, each symbol, $0, \ldots, K$, of the sequence vector $S_N$ is assumed as equally probable, simplifying the solution to the minimum distance sequence between the vector [$Y_1 \ldots Y_i \ldots Y_N$] and $X_N$ (a deterministic function of $S_N$). In other words, the sequence vector $S_N$ that minimizes the resultant distance between Y and X is chosen. In general, for a sequence vector of length N, there are $(K+1)^N$ possible solutions, making full search quickly intractable with increasing N. Fortunately, this general class of problem arises frequently in communication theory and is termed maximum-likelihood sequence detection (MLSD). Dynamic programming methods (e.g., Viterbi algorithm), produce the maximum-likelihood solution, however, because of the very deep memory in this case, it is not much better than full search in terms of storage requirements or computational complexity. Assuming K is limited to 5 and 300 nucleotide additions, this would generate a search space of $6^{300} \approx 2.8 \times 10^{233}$. This can be reduced significantly by assuming that the received sequence has a much smaller effective memory; however, even in this case the search space is prohibitive, since the effective memory quickly reaches over about 60 for 300 nucleotide additions.

While the present invention is described with reference to several particular example embodiments, those skilled in the art will recognize that many changes may be made thereto without departing from the spirit and scope of the present invention. Such changes may include, for example, sequencing polymers other than those discussed, replacing synthesis with another approach such as cleavage or replacing cleavage with another approach such as synthesis or other deconstruction-type approach, or using approaches in "Modeling and Base-Calling for DNA Sequencing-by-Synthesis". These and other approaches as described in the claims below characterize aspects of the present invention.

What is claimed is:

1. A method for DNA sequencing using a multitude of DNA specimens each having the same DNA sequence, the method comprising:
    performing at least one step in a DNA sequencing test, where each of the at least one step in the DNA sequencing test is performed on the multitude of DNA specimens and produces ideal DNA specimens and non-ideal DNA specimens, wherein, for each step in the DNA sequencing test, the ideal DNA specimens have a corresponding ideal length and the non-ideal DNA specimens have lengths that are different from the corresponding ideal length,
    for each of the at least one step in the DNA sequencing test, using a computer processor by executing instructions that cause the computer processor to:
        receive data captured from a corresponding step of the DNA sequencing test,
        determine potential distortion in the received data by modeling the potential distortion as intersymbol interference resulting from channel pulses that correspond to subgroups of DNA specimens that represent potential non-ideal DNA specimens, and
        identify, for a corresponding step, a new base by comparing the data received from the DNA sequencing test to the determined potential distortion.

2. The method of claim 1, wherein each step in the DNA sequencing test is a step in synthesis of the multitude of DNA specimens.

3. The method of claim 1, wherein each step in the DNA sequencing test is a step in cleavage of the multitude of DNA specimens.

4. The method of claim 1, wherein using the computer processor by executing instructions further causes the computer processor to determine the potential distortion by categorizing the multitude of DNA specimens into subgroups corresponding to incomplete incorporation for at least some of the multitude of DNA specimens during the DNA sequencing test.

5. The method of claim 1, wherein using the computer processor by executing instructions further causes the computer processor to determine the potential distortion by combining contributions from non-ideal DNA specimens from a previous step in the DNA sequencing test with one or more contributions from non-ideal DNA specimens that correspond to a current step in the DNA sequencing test.

6. The method of claim 1, further including identifying noise from a source other than the non-ideal DNA specimens and using the identified noise in the modeling of the potential distortion for the DNA sequencing test.

7. The method of claim 1, wherein using the computer processor by executing instructions further causes the computer processor to determine the potential distortion by summing contributions from non-ideal DNA specimens according to weighting corresponding to a fraction of DNA specimens that successfully advance in each step of the DNA sequencing test.

8. The method of claim 1, wherein using the computer processor by executing instructions further causes the computer processor to determine the potential distortion by assigning a weight corresponding to a probability of DNA specimens existing in each of the subgroups.

9. The method of claim 1, wherein using the computer processor by executing instructions further causes the computer processor to determine the potential distortion by calculating contributions from non-ideal DNA specimens independently for each base component of the multitude of DNA specimens.

10. The method of claim 1, wherein the data captured from the DNA sequencing test includes photoemission data captured during pyrosequencing.

11. The method of claim 10, wherein modeling the potential distortion as intersymbol interference resulting from channel pulses further includes normalizing the photoemission data captured during pyrosequencing based upon an integration of photoemission levels from the DNA sequencing test.

12. The method of claim 1, wherein using a computer processor to identify the new base includes applying a partial iterative maximum-likelihood sequence detection (MLSD) to the data captured from the DNA sequencing test.

13. The method of claim 1, wherein using a computer processor to identify the new base includes applying a Viterbi algorithm to the data captured from the DNA sequencing test.

14. A system for DNA sequencing via a multitude of DNA specimens each having the same DNA sequence, the system comprising:
    a polymer sequencing device that is configured to perform at least one step in a DNA sequencing test, where each of the at least one step in the DNA sequencing test is performed on the multitude of DNA specimens and produces ideal DNA specimens and non-ideal DNA specimens, wherein, for each step in the DNA sequencing test, the ideal DNA specimens have a corresponding ideal length and the non-ideal DNA specimens have lengths that are different from the corresponding ideal length; and
    logic that includes a processor and processor-readable storage medium configured with processor executable instructions that when executed and for each of the at least one step in the DNA sequencing test, cause the processor to:
        receive data captured from a corresponding step of the DNA sequencing test,
        determine potential distortion in the received data by modeling the potential distortion as intersymbol interference resulting from channel pulses that correspond to subgroups of DNA specimens that represent potential non-ideal DNA specimens, and identify, for a corresponding step, a new base by comparing the data received from the DNA sequencing test to the determined potential distortion.

15. The system of claim 14, wherein the polymer sequencing device performs one of pyrosequencing of DNA and cleaving of DNA.

16. The system of claim 14, wherein the polymer sequencing device stores data in a database for subsequent use by the logic, the data being obtained from DNA sequencing.

17. The system of claim 14, wherein the polymer sequencing device and the logic are implemented on a common device.

* * * * *